US010905883B2

(12) United States Patent
Clark et al.

(10) Patent No.: US 10,905,883 B2
(45) Date of Patent: Feb. 2, 2021

(54) METHODS AND SYSTEMS FOR SELECTING STIMULATION PARAMETERS FOR ELECTRICAL STIMULATION DEVICES

(71) Applicant: Boston Scientific Neuromodulation Corporation, Valencia, CA (US)

(72) Inventors: Bryan Allen Clark, Forest Lake, MN (US); William Conrad Stoffregen, Lake Elmo, MN (US); Michael X. Govea, Castaic, CA (US); Craig M. Stolen, New Brighton, MN (US); David J. Ternes, Roseville, MN (US); David Blum, Boston, MA (US); Pramodsingh Hirasingh Thakur, Woodbury, MN (US); Stephen B. Ruble, Lino Lakes, MN (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 480 days.

(21) Appl. No.: 15/829,769

(22) Filed: Dec. 1, 2017

(65) Prior Publication Data
US 2018/0154156 A1 Jun. 7, 2018

Related U.S. Application Data

(60) Provisional application No. 62/429,650, filed on Dec. 2, 2016.

(51) Int. Cl.
*A61N 1/36* (2006.01)
*A61N 1/368* (2006.01)
(Continued)

(52) U.S. Cl.
CPC ..... *A61N 1/36185* (2013.01); *A61N 1/36053* (2013.01); *A61N 1/3686* (2013.01);
(Continued)

(58) Field of Classification Search
CPC ............ A61N 1/36185; A61N 1/36053; A61N 1/36171; A61N 1/36175; A61N 1/36178;
(Continued)

(56) References Cited

U.S. PATENT DOCUMENTS 3,769,984 A    11/1973   Muench
3,941,136 A    3/1976    Bucalo
(Continued)

FOREIGN PATENT DOCUMENTS

EP    0234457    9/1987
EP    0778047    6/1997
(Continued)

OTHER PUBLICATIONS

Rattay, F., "Analysis of Models for External Stimulation of Axons," IEEE Transactions on Biomedical Engineering, BME-33(10): 974-977, 1986.
(Continued)

*Primary Examiner* — Catherine M Voorhees
*Assistant Examiner* — Roland Dinga
(74) *Attorney, Agent, or Firm* — Branch Partners PLLC; Bruce E. Black

(57) ABSTRACT

Methods and systems for selecting electrical stimulation parameters for an electrical stimulation device implanted in a patient can use an iterative process for identifying electrodes for stimulation, as well as suitable stimulation parameters. The process begins with an initial set of electrode combinations to identify regions of the nerve or other tissue for stimulation. This leads to selection of other electrode combinations to test, followed by the selection of multiple electrode groups (which can include three or more electrodes) for stimulation.

20 Claims, 10 Drawing Sheets

(51) Int. Cl.
  *A61N 1/37* (2006.01)
  *A61N 1/08* (2006.01)
  *A61N 1/05* (2006.01)
  *A61N 1/372* (2006.01)
  *A61N 1/378* (2006.01)

(52) U.S. Cl.
  CPC ..... *A61N 1/36171* (2013.01); *A61N 1/36175* (2013.01); *A61N 1/36178* (2013.01); *A61N 1/3706* (2013.01); *A61N 1/0556* (2013.01); *A61N 1/086* (2017.08); *A61N 1/3787* (2013.01); *A61N 1/37223* (2013.01)

(58) Field of Classification Search
  CPC .... A61N 1/3686; A61N 1/3706; A61N 1/086; A61N 1/0556; A61N 1/37223; A61N 1/3787
  See application file for complete search history.

(56) References Cited

U.S. PATENT DOCUMENTS

| | | |
|---|---|---|
| 4,033,357 A | 7/1977 | Helland et al. |
| 4,135,518 A | 1/1979 | Dutcher |
| 4,257,428 A | 3/1981 | Barton et al. |
| 4,301,815 A | 11/1981 | Doring |
| 4,409,994 A | 10/1983 | Doring |
| 4,475,560 A | 10/1984 | Tarjan et al. |
| 4,506,679 A | 3/1985 | Mann |
| 4,542,753 A | 9/1985 | Brenman et al. |
| 4,585,005 A | 4/1986 | Lue et al. |
| 4,628,944 A | 12/1986 | MacGregor et al. |
| 4,702,254 A | 10/1987 | Zabara |
| 4,716,888 A | 1/1988 | Wesner |
| 4,722,353 A | 2/1988 | Sluetz |
| 4,796,643 A | 1/1989 | Nakazawa et al. |
| 4,867,164 A | 9/1989 | Zabara |
| 4,920,979 A | 5/1990 | Bullara |
| 4,934,368 A | 6/1990 | Lynch |
| 4,957,118 A | 9/1990 | Erlebacher |
| 5,025,807 A | 6/1991 | Zabara |
| 5,095,905 A | 3/1992 | Klepinski |
| 5,139,539 A | 8/1992 | Haynes, Jr. |
| 5,143,067 A | 9/1992 | Rise et al. |
| 5,193,539 A | 3/1993 | Schulman et al. |
| 5,193,540 A | 3/1993 | Schulman et al. |
| 5,239,540 A | 8/1993 | Rovira et al. |
| 5,251,634 A | 10/1993 | Weinberg |
| 5,257,634 A | 11/1993 | Kroll |
| 5,282,468 A | 2/1994 | Klepinski |
| 5,312,439 A | 5/1994 | Loeb |
| 5,314,457 A | 5/1994 | Jeutter et al. |
| 5,324,322 A | 6/1994 | Grill et al. |
| 5,324,327 A | 6/1994 | Cohen |
| 5,376,108 A | 12/1994 | Collins et al. |
| 5,405,367 A | 4/1995 | Schulman et al. |
| 5,433,735 A | 7/1995 | Zanakis et al. |
| 5,439,938 A | 8/1995 | Snyder et al. |
| 5,454,840 A | 10/1995 | Krakovsky et al. |
| 5,480,420 A | 1/1996 | Hoegnelid et al. |
| 5,487,756 A | 1/1996 | Kallesoe et al. |
| 5,531,781 A | 7/1996 | Alferness et al. |
| 5,571,118 A | 11/1996 | Boutos |
| 5,741,319 A | 4/1998 | Woloszko et al. |
| 5,755,762 A | 5/1998 | Bush |
| 5,775,331 A | 7/1998 | Raymond et al. |
| 5,871,530 A | 2/1999 | Williams et al. |
| 5,876,399 A | 3/1999 | Chia et al. |
| 5,919,220 A | 7/1999 | Stieglitz et al. |
| 5,919,222 A | 7/1999 | Hjelle et al. |
| 5,922,015 A | 7/1999 | Schaldach et al. |
| 5,938,584 A | 8/1999 | Ardito et al. |
| 6,051,017 A | 4/2000 | Loeb et al. |
| 6,058,332 A | 5/2000 | Dahl |
| 6,061,596 A | 5/2000 | Richmond et al. |
| 6,151,526 A | 11/2000 | Tziviskos |
| 6,175,710 B1 | 1/2001 | Kamaji et al. |
| 6,175,764 B1 | 1/2001 | Loeb et al. |
| 6,181,965 B1 | 1/2001 | Loeb et al. |
| 6,181,969 B1 | 1/2001 | Fielding et al. |
| 6,181,973 B1 | 1/2001 | Ceron et al. |
| 6,185,452 B1 | 2/2001 | Schulman et al. |
| 6,185,455 B1 | 2/2001 | Loeb et al. |
| 6,188,932 B1 | 2/2001 | Lindegren |
| 6,201,994 B1 | 3/2001 | Warman et al. |
| 6,214,032 B1 | 4/2001 | Loeb et al. |
| 6,224,450 B1 | 5/2001 | Norton |
| 6,271,094 B1 | 8/2001 | Boyd et al. |
| 6,278,897 B1 | 8/2001 | Rutten et al. |
| 6,292,703 B1 | 9/2001 | Meier et al. |
| 6,295,944 B1 | 10/2001 | Lovett |
| 6,308,105 B1 | 10/2001 | Duysens et al. |
| 6,315,721 B2 | 11/2001 | Schulman et al. |
| 6,364,278 B1 | 4/2002 | Lin et al. |
| 6,391,985 B1 | 5/2002 | Goode et al. |
| 6,456,866 B1 | 9/2002 | Tyler et al. |
| 6,463,335 B1 | 10/2002 | Munch et al. |
| 6,516,227 B1 | 2/2003 | Meadows et al. |
| 6,582,441 B1 | 6/2003 | He et al. |
| 6,584,363 B2 | 6/2003 | Heil, Jr. et al. |
| 6,609,029 B1 | 8/2003 | Mann et al. |
| 6,609,032 B1 | 8/2003 | Woods et al. |
| 6,643,546 B2 | 11/2003 | Mathis et al. |
| 6,650,943 B1 | 11/2003 | Whitehurst et al. |
| 6,735,474 B1 | 5/2004 | Loeb et al. |
| 6,741,892 B1 | 5/2004 | Meadows et al. |
| 6,788,975 B1 | 9/2004 | Whitehurst et al. |
| 7,003,352 B1 | 2/2006 | Whitehurst |
| 7,006,875 B1 | 2/2006 | Kuzma et al. |
| 7,203,548 B2 | 4/2007 | Whitehurst et al. |
| 7,244,150 B1 | 7/2007 | Brase et al. |
| 7,248,930 B1 | 7/2007 | Woloszko et al. |
| 7,292,890 B2 | 11/2007 | Whitehurst et al. |
| 7,437,193 B2 | 10/2008 | Parramon et al. |
| 7,450,997 B1 | 11/2008 | Pianca et al. |
| 7,460,913 B2 | 12/2008 | Kuzma et al. |
| 7,584,004 B2 | 9/2009 | Caparso et al. |
| 7,596,414 B2 | 9/2009 | Whitehurst et al. |
| 7,610,103 B2 | 10/2009 | Whitehurst et al. |
| 7,672,734 B2 | 3/2010 | Anderson et al. |
| 7,706,892 B2 | 4/2010 | Colvin et al. |
| 7,761,165 B1 | 7/2010 | He et al. |
| 7,783,359 B2 | 8/2010 | Meadows |
| 7,783,362 B2 | 8/2010 | Whitehurst et al. |
| 7,792,590 B1 | 9/2010 | Pianca et al. |
| 7,809,446 B2 | 10/2010 | Meadows |
| 7,840,279 B2 | 11/2010 | He |
| 7,949,395 B2 | 5/2011 | Kuzma |
| 7,953,498 B1 | 5/2011 | Carbunaru et al. |
| 7,974,706 B2 | 7/2011 | Moffitt et al. |
| 8,019,443 B2 | 9/2011 | Schleicher et al. |
| 8,155,757 B1 | 4/2012 | Neisz et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,483,237 B2 | 7/2013 | Zimmermann et al. |
| 8,594,805 B2 | 11/2013 | Hincapie Ordonez et al. |
| 8,612,025 B2 | 12/2013 | Neisz et al. |
| 8,688,235 B1 | 4/2014 | Pianca et al. |
| 8,718,790 B2 | 5/2014 | Pianca |
| 8,768,488 B2 | 7/2014 | Barker |
| 8,818,524 B2 | 8/2014 | Hincapie Ordonez et al. |
| 8,831,742 B2 | 9/2014 | Pianca et al. |
| 8,849,422 B2 | 9/2014 | Pianca |
| 8,934,992 B2 | 1/2015 | Johnson et al. |
| 2003/0040785 A1 | 2/2003 | Maschino et al. |
| 2003/0045919 A1 | 3/2003 | Swoyer et al. |
| 2003/0074039 A1 | 4/2003 | Puskas |
| 2003/0078623 A1 | 4/2003 | Weinberg et al. |
| 2003/0114905 A1 | 6/2003 | Kuzma |
| 2003/0199938 A1 | 10/2003 | Smits et al. |

(56) References Cited

U.S. PATENT DOCUMENTS

| | | |
|---|---|---|
| 2003/0236558 A1 | 12/2003 | Whitehurst et al. |
| 2004/0010303 A1 | 1/2004 | Bolea et al. |
| 2004/0034401 A1 | 2/2004 | Dahlberg et al. |
| 2004/0049240 A1 | 3/2004 | Gerber et al. |
| 2004/0059392 A1 | 3/2004 | Parramon et al. |
| 2004/0111139 A1 | 6/2004 | McCreery |
| 2004/0230280 A1 | 11/2004 | Cates et al. |
| 2005/0010265 A1 | 1/2005 | Baru Fassio et al. |
| 2005/0065589 A1 | 3/2005 | Schneider et al. |
| 2005/0177220 A1 | 8/2005 | Iaizzo et al. |
| 2005/0182472 A1 | 8/2005 | Wahlstrom et al. |
| 2006/0161204 A1 | 7/2006 | Colvin et al. |
| 2006/0184204 A1 | 8/2006 | He |
| 2006/0212075 A1 | 9/2006 | Marnfeldt |
| 2006/0241737 A1 | 10/2006 | Tockman et al. |
| 2006/0282145 A1 | 12/2006 | Caparso et al. |
| 2007/0150036 A1 | 6/2007 | Anderson |
| 2007/0219595 A1 | 9/2007 | He |
| 2008/0046055 A1 | 2/2008 | Durand et al. |
| 2008/0071320 A1 | 3/2008 | Brase |
| 2009/0043352 A1 | 2/2009 | Brooke et al. |
| 2009/0118727 A1 | 5/2009 | Pearson et al. |
| 2009/0187222 A1 | 7/2009 | Barker |
| 2009/0210042 A1 | 8/2009 | Kowalczewski |
| 2009/0275956 A1* | 11/2009 | Burnes ............... A61N 1/05 606/129 |
| 2009/0276021 A1 | 11/2009 | Meadows et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2010/0049276 A1 | 2/2010 | Blum et al. |
| 2010/0076535 A1 | 3/2010 | Pianca et al. |
| 2010/0114202 A1 | 5/2010 | Donofrio et al. |
| 2010/0168831 A1 | 7/2010 | Korivi et al. |
| 2010/0241207 A1 | 9/2010 | Bluger |
| 2010/0268298 A1 | 10/2010 | Moffitt et al. |
| 2010/0298916 A1 | 11/2010 | Rabischong et al. |
| 2010/0312320 A1 | 12/2010 | Faltys et al. |
| 2011/0004267 A1 | 1/2011 | Meadows et al. |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130817 A1 | 6/2011 | Chen |
| 2011/0130818 A1 | 6/2011 | Chen |
| 2011/0160810 A1* | 6/2011 | Griffith ............ A61N 1/37223 607/72 |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0078320 A1* | 3/2012 | Schotzko ........... A61N 1/37276 607/17 |
| 2012/0165898 A1* | 6/2012 | Moffitt .............. A61N 1/37247 607/45 |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0277819 A1 | 11/2012 | Cowley et al. |
| 2012/0316615 A1 | 12/2012 | Digiore et al. |
| 2013/0023974 A1 | 1/2013 | Amrani |
| 2013/0105071 A1 | 5/2013 | Digiore et al. |
| 2013/0172973 A1 | 7/2013 | Tockman et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317518 A1 | 11/2013 | Govea |
| 2013/0317587 A1 | 11/2013 | Barker |
| 2013/0325091 A1 | 12/2013 | Pianca et al. |
| 2013/0338733 A1 | 12/2013 | Goddard et al. |
| 2014/0039587 A1 | 2/2014 | Romero |
| 2014/0074213 A1 | 3/2014 | Neisz et al. |
| 2014/0128950 A1 | 5/2014 | Thota et al. |
| 2014/0228905 A1 | 8/2014 | Bolea |
| 2014/0277284 A1 | 9/2014 | Chen et al. |
| 2014/0353001 A1 | 12/2014 | Romero et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0202433 A1 | 7/2015 | Franke et al. |
| 2015/0202446 A1 | 7/2015 | Franke et al. |
| 2015/0366467 A1 | 12/2015 | De Kock et al. |
| 2016/0136443 A1* | 5/2016 | Grandhe ............... G16H 20/40 607/60 |
| 2017/0224982 A1 | 8/2017 | Nageri et al. |

FOREIGN PATENT DOCUMENTS

| | | |
|---|---|---|
| WO | 98/37926 | 9/1998 |
| WO | 98/43700 | 10/1998 |
| WO | 98/43701 | 10/1998 |
| WO | 2008019483 | 2/2008 |
| WO | 2008048471 | 4/2008 |
| WO | 2013188871 | 12/2013 |

OTHER PUBLICATIONS

U.S. Appl. No. 15/601,838, filed May 22, 2017.
U.S. Appl. No. 15/436,544, filed Feb. 17, 2017.
U.S. Appl. No. 62/429,650, filed Dec. 2, 2016.
U.S. Appl. No. 15/656,734, filed Jul. 21, 2017.
Rozman et al., "Selective Stimulation of Autonomic Nerves and Recording of Electroneurograms in a Canine Model," Artificial Organs, 21(8): 592-596, 2008.
Polasek et al., "Stimuiation Stability and Selectivity of Chronically Implanted Multicontact Nerve Cuff Electrodes in the Human Upper Extremity,"IEEE Transactions on Neural Systems and Rehabilitation Engineering, vol. 17, No. 5, 428-437, Oct. 2009.
Plachta et al., "Blood pressure control with selective vagal nerve stimulation and minimal side effects," J. Neural Eng. 11 (2014) 036011 (15pp), 2014.
International Search Report and Written Opinion for PCT/US2017/064346 dated Mar. 16, 2018.

* cited by examiner

METHODS AND SYSTEMS FOR SELECTING STIMULATION PARAMETERS FOR ELECTRICAL STIMULATION DEVICES

CROSS-REFERENCE TO RELATED APPLICATIONS

This application claims the benefit under 35 U.S.C. § 119(e) of U.S. Provisional Patent Application Ser. No. 62/429,650, filed Dec. 2, 2016, which is incorporated herein by reference.

FIELD

The present invention is directed to the area of implantable electrical stimulation systems and methods of making and using the systems. The present invention is also directed to methods and systems for selecting stimulation parameters for implantable electrical stimulation devices, as well as closed-loop electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a method of selecting electrical stimulation parameters for an electrical stimulation device implanted in a patient, the electrical stimulation device including an electrical stimulation lead including a plurality of electrodes. The method includes, for each of a plurality of first electrode combinations, receiving at least one value indicative of electrical stimulation using the first electrode combination, wherein each of the first electrode combinations includes at least two electrodes of the electrical stimulation lead; based on the received values indicative of electrode stimulation using the first electrode combinations, selecting one or more of the first electrode combinations; selecting a plurality of second electrode combinations including the selected one or more of the first electrode combinations and one or more additional electrode combinations, wherein at least one of the additional electrode combinations includes at least one electrode from the selected one or more of the first electrode combinations, wherein each of the second electrode combinations includes at least two electrodes of the electrical stimulation lead; for each of the plurality of second electrode combinations, receiving at least one value indicative of electrical stimulation using the second electrode combination; based on the received values indicative of electrode stimulation using the second electrode combinations, selecting one or more of the second electrode combinations; for each of the selected one or more of the second electrode combinations, receiving values indicative of electrical stimulation using different sets of stimulation parameters with the selected one or more of the second electrode combinations; based on the values indicative of the electrical stimulation using the different sets of stimulation parameters, selecting at least one third electrode combination that includes two or more electrodes of the electrical stimulation lead; for each of the selected at least one third electrode combination, receiving values indicative of electrical stimulation using different sets of stimulation parameters with the selected at least one third electrode combination; based on the values indicative of the electrical stimulation using the different sets of stimulation parameters, selecting one of the at least one third electrode combination as a final electrode group and selecting one of the sets of stimulation parameters for the final electrode group; and initiating a signal to the electrical stimulation device implanted in the patient, the signal indicating the final electrode group and the selected set of stimulation parameters to be used with the final electrode group for electrical stimulation of the patient through the electrical stimulation lead using the final electrode group and the selected set of stimulation parameters.

In at least some embodiments, the method further includes stimulating the patient using the final electrode group and the selected set of stimulation parameters.

In at least some embodiments, the method further includes, based on the values indicative of the electrical stimulation using the different sets of stimulation parameters, selecting one of the at least one third electrode combination as a second final electrode group and selecting one of the sets of stimulation parameters for the second final electrode group; and initiating a signal to the electrical stimulation device implanted in the patient, the signal indicating the second final electrode group and the selected set of stimulation parameters to be used with the second final electrode group for electrical stimulation of the patient through the electrical stimulation lead using the second final electrode group and the selected set of stimulation parameters. In at least some embodiments, the method further includes stimulating the patient using the final electrode group and the selected set of stimulation parameters for the final electrode group; and switching to stimulating the patient using the second final electrode group and the selected set of stimulation parameters for the second final electrode group. In at least some embodiments, the method further includes alternating between stimulating the patient using the final electrode group and the selected set of stimulation parameters for the final electrode group and stimulating the patient using the second final electrode group and the selected set of stimulation parameters for the second final electrode group.

In at least some embodiments, receiving at least one value indicative of electrical stimulation using the first electrode combination includes receiving from the patient an indication of a threshold stimulation amplitude, wherein stimulation at tested stimulation amplitudes below the threshold stimulation amplitude is tolerable to the patient, but stimulation at the threshold stimulation amplitude is not tolerable to the patient. In at least some embodiments, receiving at least one value indicative of electrical stimulation using the first electrode combination includes receiving from the patient an indication of a threshold stimulation amplitude, wherein stimulation at tested stimulation amplitudes above the threshold stimulation amplitude is not tolerable to the patient, but stimulation at the threshold stimulation amplitude is tolerable to the patient.

In at least some embodiments, the set of stimulation parameters includes at least one of stimulation amplitude, pulse frequency, pulse duration, duty cycle, pulse waveform, electrode polarity, or burst frequency. In at least some embodiments, at least one of the at least one third electrode combination includes at least three electrodes, wherein either a) at least two electrodes are anodes or b) at least two electrodes are cathodes or c) both a) and b). In at least some embodiments, at least one of the at least one third electrode combination includes an electrode including a case of a control unit of the electrical stimulation device.

In at least some embodiments, each of the at least one third electrode combination includes at least two electrodes of a one of the selected one or more of the second electrode combinations. In at least some embodiments, no electrode of the electrical stimulation lead is part of more than two of the first electrode combinations.

Another embodiment is a system for selecting stimulation parameters for electrical stimulation. The system includes a processor configured and arranged to perform any of the methods described above. In at least some embodiments, the system further includes an implantable stimulation device configured and arranged to stimulate the patient using the final electrode group and the selected set of stimulation parameters for the final electrode group.

Yet another embodiment is a non-transitory computer-readable medium having processor-executable instructions for selecting stimulation parameters for electrical stimulation. The processor-executable instructions, when installed onto a device, enable the device to perform any of the methods described above.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to methods and systems for selecting stimulation parameters for implantable electrical stimulation cuff devices.

Suitable implantable electrical stimulation systems include, but are not limited to, a least one lead with one or more electrodes disposed along a distal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,203,548; 7,244,150; 7,450,997; 7,596,414; 7,610,103; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference in their entireties. Below the leads, systems, and methods will be illustrated using a cuff lead for peripheral nerve stimulation. It will be understood, however, that other leads can be used including, but not limited to, percutaneous and directional leads and paddle leads. It will also be understood that the leads, systems, and methods described herein can also be used for other types of stimulation including, but not limited to, spinal cord stimulation, deep brain stimulation, dorsal root ganglion stimulation, and stimulation of other nerves, organs, or tissues.

Figure 1:
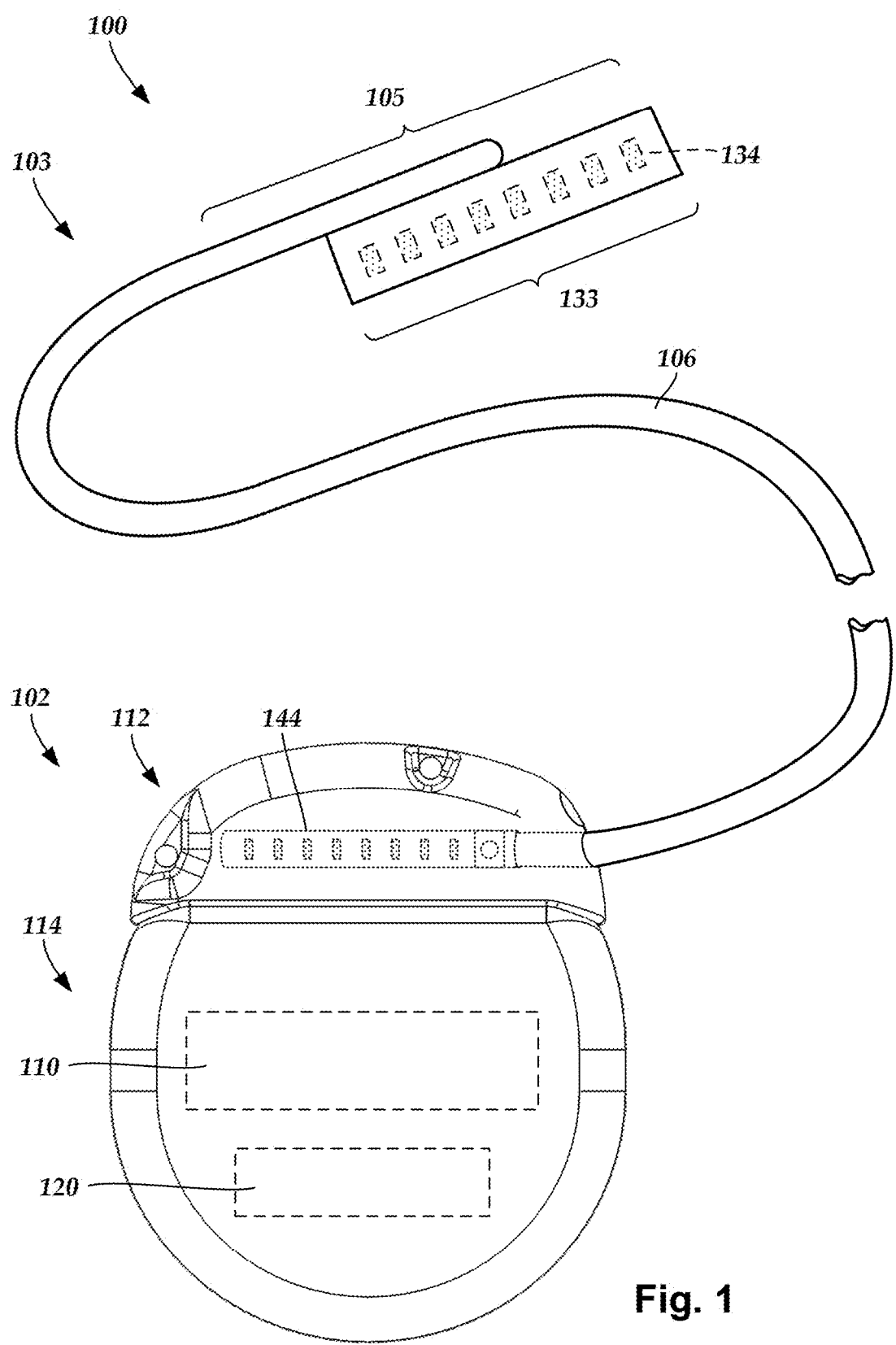
FIG. 1 is a schematic view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a distal end portion 105, shown schematically, but will be described in detail below (e.g., a distal end portion 300 in FIGS. 3A-3D.) The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. Stimulation circuitry 110 and an optional power source 120 are disposed in the electronics housing 114. A control module connector 144 is disposed in the connector housing 112. The control module connector 144 is configured and arranged to make an electrical connection between the lead 103 and the stimulation circuitry 110 of the control module 102.

The electrical stimulation system or components of the electrical stimulation system, including the lead body 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the lead body 106 are typically disposed in, or separated by, a non-conductive, biocompatible material such as, for example, silicone, polyurethane, polyetheretherketone ("PEEK"), epoxy, and the like or combinations thereof. The lead body 106 may be formed in the desired shape by any process including, for example, molding (including injection molding), casting, and the like. The non-conductive material typically extends from the distal end of the lead body 106 to the proximal end of the lead body 106.

Figure 2A:
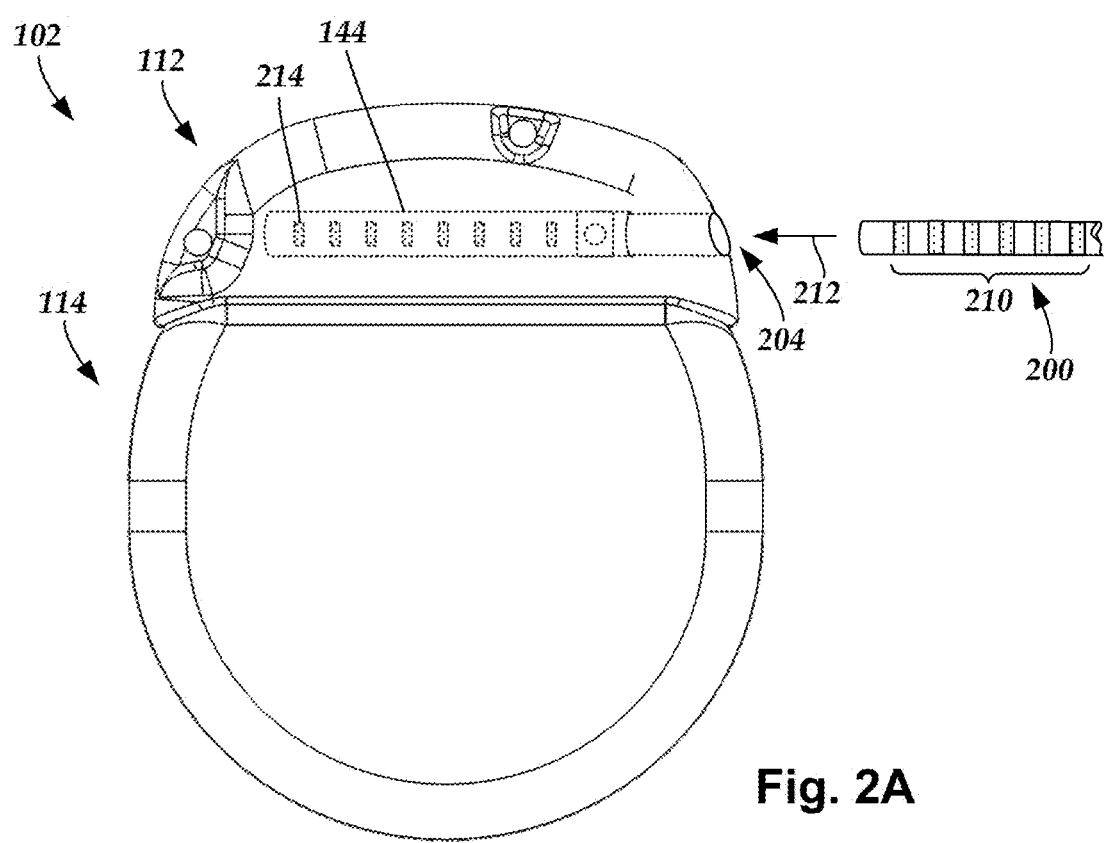
FIG. 2A is a schematic view of one embodiment of the control module of FIG. 1 configured and arranged to electrically couple to an elongated device, according to the invention.
Figure 2B:
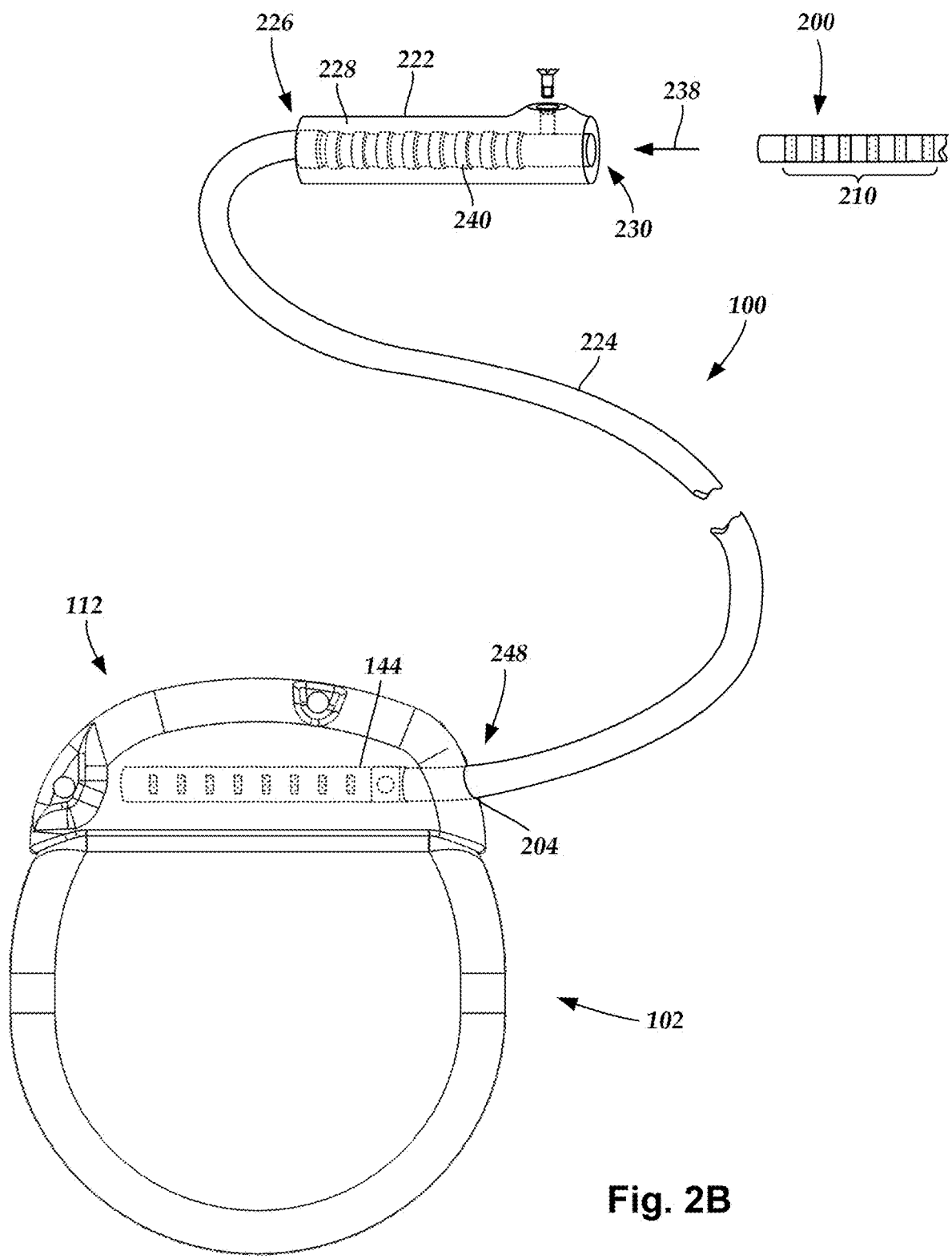
FIG. 2B is a schematic view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the lead body 106 of the electrical stimulation system 100 (as well as any splitters, lead extensions, adaptors, or the like) for electrical connection to corresponding connector contacts (e.g., 214 and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like).

Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the lead body 106. In at least one embodiment, the one or more lumens are flushed continually, or on a regular basis, with saline, cerebrospinal fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the lead extension 224 of FIG. 2B, an adaptor, or the like or combinations thereof), or a combination thereof.

The control module connector 144 defines at least one port into which a proximal end of the elongated device 200 can be inserted, as shown by directional arrow 212. In FIG. 2A (and in other figures), the connector housing 112 is shown having one port 204. The connector housing 112 can define any suitable number of ports including, for example, one, two, three, four, five, six, seven, eight, or more ports.

The control module connector 144 also includes a plurality of connector contacts, such as connector contact 214, disposed within each port 204. When the elongated device 200 is inserted into the port 204, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

In at least some instances, a large control module, such as the control module 102 illustrated in FIGS. 1-2B, is not desirable. A smaller, more compact control module may be suitable for situations such as, for example, short-term implantation (for example, 1 or 2 weeks, 1, 2, 3, 4, 6, 8, 12, or 18 months), short-term trial (for example, 1 or 2 weeks, 1, 2, 3, 4, 6, 8, 12, or 18 months), clinical studies (for example, for a period of 1 or 2 weeks, 1, 2, 3, 4, 6, 8, 12, or 18 months), or the like. Such a control module may also be useful when a less invasive surgical implantation is desired, recommended, or required. In some instances, a patient or clinician may be willing to charge the control module more frequently if the control module is smaller or the surgery is less invasive. In addition, there may be more options in the body of the patient for implantation of a smaller control module than are available for the larger control module (which is often implanted in the thoracic body cavity or the buttocks due to the size of the device.) A smaller control module may also be less expensive and particularly useful for trials to determine whether electrical stimulation is beneficial. In at least some embodiments, the electrical stimulation system with the smaller control module can be upgraded to an electrical stimulation system such as that illustrated in FIGS. 1-2B if the trial shows sufficient benefit to the patient. In at least some embodiments, the smaller control module may allow for the device to be MRI (magnetic resonance imaging) conditionally safe because of its implant location and size.

In some embodiments, the control module can be made smaller by permanently affixing the lead (or a lead extension) to the control module. For example, the lead can be hardwired to the stimulation circuitry so that the control module does not need a connector and header.

Figure 3A:
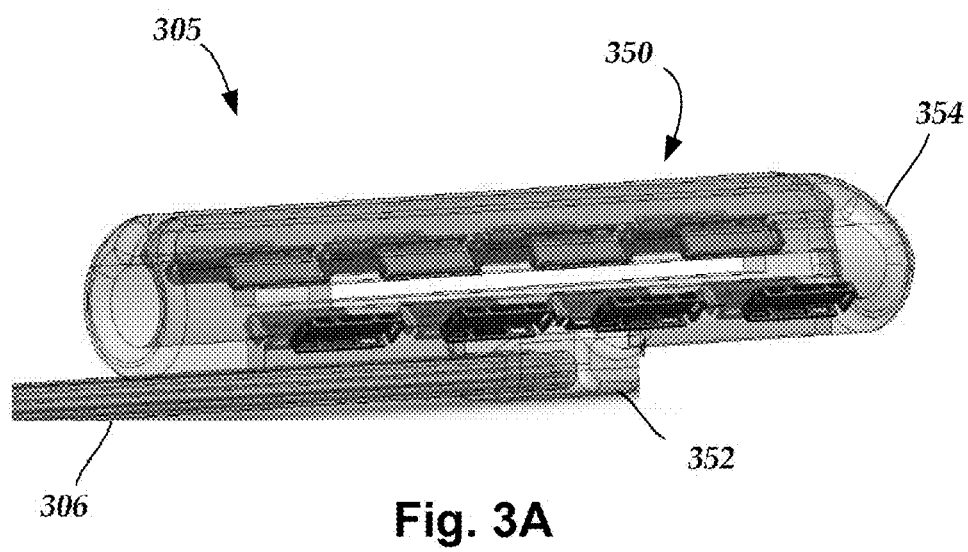
FIG. 3A is a schematic perspective view of a distal end portion of a lead that includes a stimulation cuff, according to the invention.

FIG. 3A illustrates, schematically, a distal end portion 305 of the lead 103 (FIG. 1) that includes a cuff 350 with a cuff body 354, a mount 352 and a lead body 306 according to an embodiment of the present invention. The lead body 306 can be, for example, structurally the same or similar to the lead body 106 (FIG. 1), operates in a same or similar manner, and may be manufactured in accordance with one or more of the methods disclosed in U.S. Patent Application No. 2007/0150036, which is hereby incorporated by reference in its entirety, or in accordance with other methods or references cited herein.

In at least some embodiments, the cuff 350 permits stimulation of a target nerve (not shown), for example a peripheral nerve located in soft tissue, and may be small in diameter. By way of example, the cuff 350 can operate to provide vagus or sympathetic nerve stimulation. When using many conventional leads to stimulate the target nerve, it may be difficult to initiate and maintain contact between the conventional lead and the target nerve. In at least some embodiments, the cuff 350 may advantageously permit an easier implantation around the target nerve than conventional cuff leads that wrap helically around the target nerve. In at least some embodiments, the cuff 350 may also permit selective stimulation of different regions of the target nerve. The number of electrodes 334 as well as the arrangement of the electrodes 334 can vary depending on the type of nerve being stimulated, a region of the nerve being stimulated, or any combination thereof.

The electrodes 334 can be formed using any conductive, biocompatible material. Examples of suitable materials include metals, alloys, conductive polymers, conductive carbon, and the like, as well as combinations thereof. In at least some embodiments, one or more of the electrodes 334 are formed from one or more of: platinum, platinum iridium, palladium, palladium rhodium, or titanium. The electrodes 334 may take the form of segmented electrodes, have a variety of shapes such as, but not limited to, a concave, convex or otherwise curved shape, a box shape, a dish or parabolic shape, or any combination thereof. In at least some embodiments, the electrodes 334 may take the form of segmented electrodes having a shape complementary to a body or carrier onto which they are disposed.

Any suitable number of electrodes 334 can be disposed on the cuff body 354 including, for example, four, five, six, seven, eight, nine, ten, eleven, twelve, fourteen, sixteen, twenty-four, thirty-two, or more electrodes 334. The electrodes 334 may be arranged into columns or rows. In at least some embodiments, one column includes four electrodes 334. The arrangement of the electrode(s) 334 may vary. For example, the electrodes 334 may be arranged in two or more parallel columns where such columns can be aligned or staggered from one another, or in any other desired column or row arrangement. The electrodes may also be arranged, for example, in a row, or "in line," along the longitudinal axis of a small diameter lead body. Optionally, the electrodes may be placed linearly, circularly, or elliptically. The arrangement of electrodes may be symmetrical or asymmetrical. As will be recognized, other arrangements of electrodes are also possible.

The electrodes 334 can be disposed on the cuff body 354 in any suitable arrangement. In at least some embodiments, an inward facing surface of the electrode 334 is flush with an inner surface of the cuff body 354. In yet other embodiments, the inward facing surface of the electrode 334 is recessed relative to the inner surface of the cuff body 354.

The lead body 306, cuff body 354 and the mount 352 can be made from a non-conductive, biocompatible material such as, for example, silicone, polyurethane, polyetheretherketone ("PEEK"), epoxy, and the like or combinations thereof. The lead body 306 and the cuff body 354 may be formed in the desired shape by any process including, for example, molding (including injection molding), casting, and the like.

In at least some embodiments, the cuff body 354 is made from silicone with electrodes 334 disposed in the silicone cuff body 354. The cuff 350 may be manufactured by molding the electrodes 334 into the cuff body 354 while allowing for electrode alignment. In an initial step, the electrodes 334 are molded into a thin, silicone carrier that allows for electrode alignment. Next, conductors (not shown) from the lead body 306 are connected (e.g., welded) to a backside of the electrodes 334. Lastly, the carrier is wrapped around a pin or rod and then overmolded into the cuff body 354.

In at least some embodiments, the conductors (not shown) from within the lead body 306 are received in the mount 352, which in turn is attached to the cuff body 354 such that each conductor passes through the mount 352 for a direct electrical connection with one of the electrodes 334 (e.g., one conductor is electrically connected with one electrode and so on). The mount 352 may be attached using a variety of means such as, but not limited to, molding or adhering the mount 352 to the cuff body 354. In other embodiments, the conductors from within the lead body 306 are electrically coupled to the electrodes 334 using jumper, intermediate or transition wires from the lead body 306 to the electrodes 334.

Figure 3B:
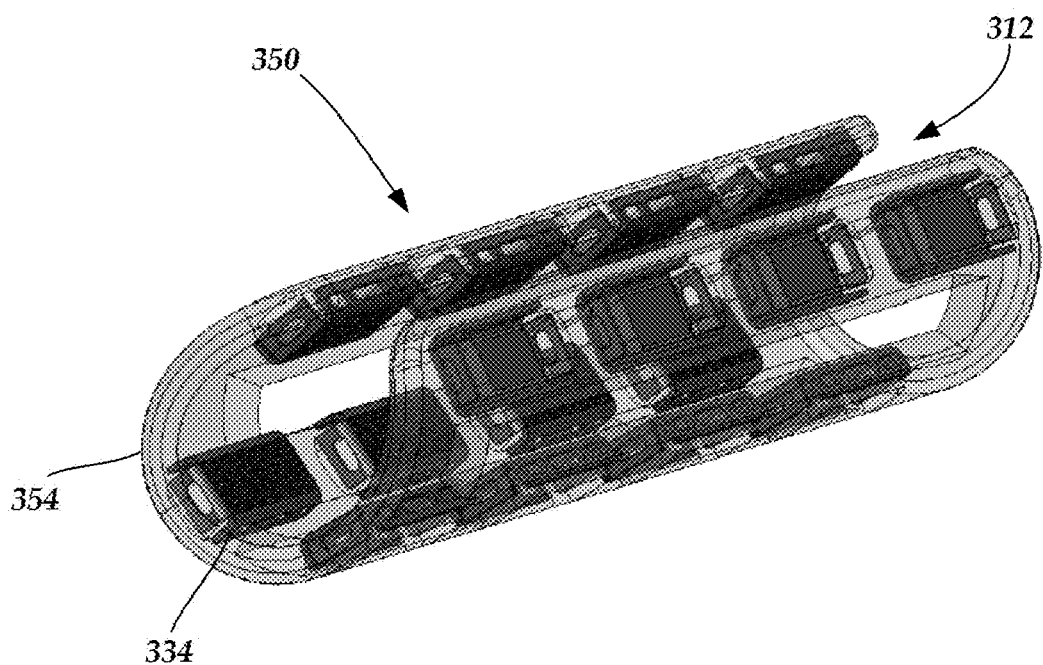
FIG. 3B is a schematic, perspective close-up view of the cuff of FIG. 3A, according to the invention.
Figure 3C:
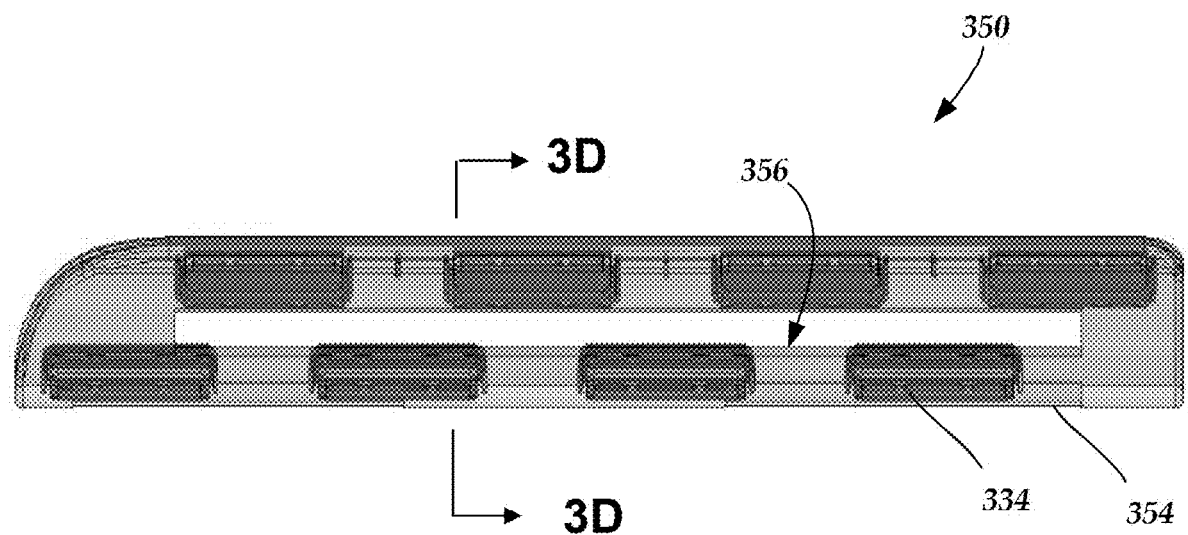
FIG. 3C is a side elevational view of the cuff of FIG. 3B, according to the invention.
Figure 3D:
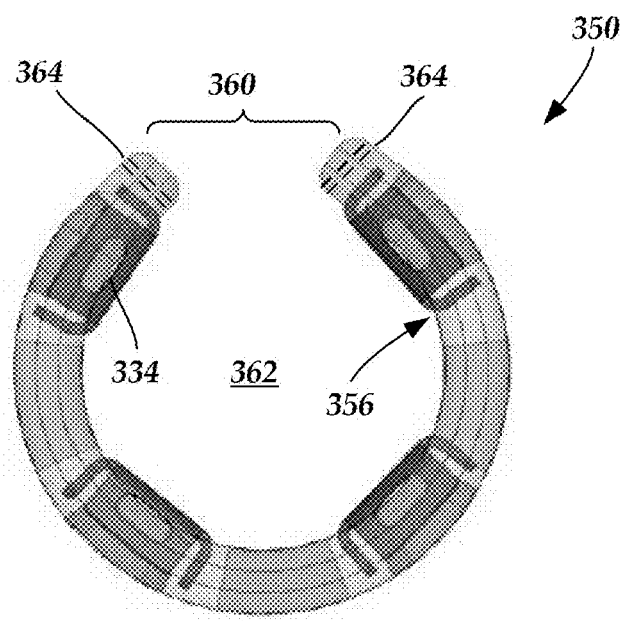
FIG. 3D is a cross-sectional view of the cuff of FIG. 3B taken along line 3D-3D, according to the invention.

FIGS. 3B-3D show the cuff 350 having the plurality of electrodes 334 disposed on an inner surface 356 of the cuff body 354. In the illustrated embodiment of FIG. 3B, the cuff body 354 takes the form of a C-shaped cuff having the inner surface 356, an outer surface 358, and a longitudinal opening 360 that extends through both the outer surface 358 and inner surface 356 of the cuff body 354. As noted above, formation of the cuff 350 into the "C-shape" can include the steps of wrapping and overmolding to form the cuff body 354 in which the inner surface 356 defines a nerve channel 362 (best seen in FIG. 3D).

The opening 360 is manipulated or initially sized to allow the target nerve (not shown) to be slipped, inserted, fed or otherwise received into nerve channel 362 of the cuff 350 such that the cuff 350 wraps around the target nerve. In at least some embodiments, the opening 360 allows the cuff 350 to be easily moved over and around the target nerve or relative to the target nerve whether rotationally or transitionally. By way of example, the cuff 350 may be rotated, translated or otherwise repositioned, if needed, along a target nerve axis 470 (FIG. 4B) that is parallel to or approximately parallel to a longitudinal axis of the nerve channel 362. Repositioning of the cuff 350 may permit intimate or selected stimulation between a particular region of the target nerve and one or more of the electrodes 334.

In at least some embodiments, once the cuff 350 has been placed in a desired position relative to the target nerve, the edges of the cuff body 354 defining the opening 360 can be sutured to capture the target nerve without undesirably compressing the target nerve. In at least some embodiments, suture holes 364 (FIG. 3D) are optionally incorporated into the edges of the cuff 350 to allow for closing or partially closing the cuff 350 around the target nerve. Moreover, at least in some embodiments, the suture holes 364 can be used as points of manipulation or tool attachment during implantation (e.g., using forceps or an equivalent tool).

Figure 4:
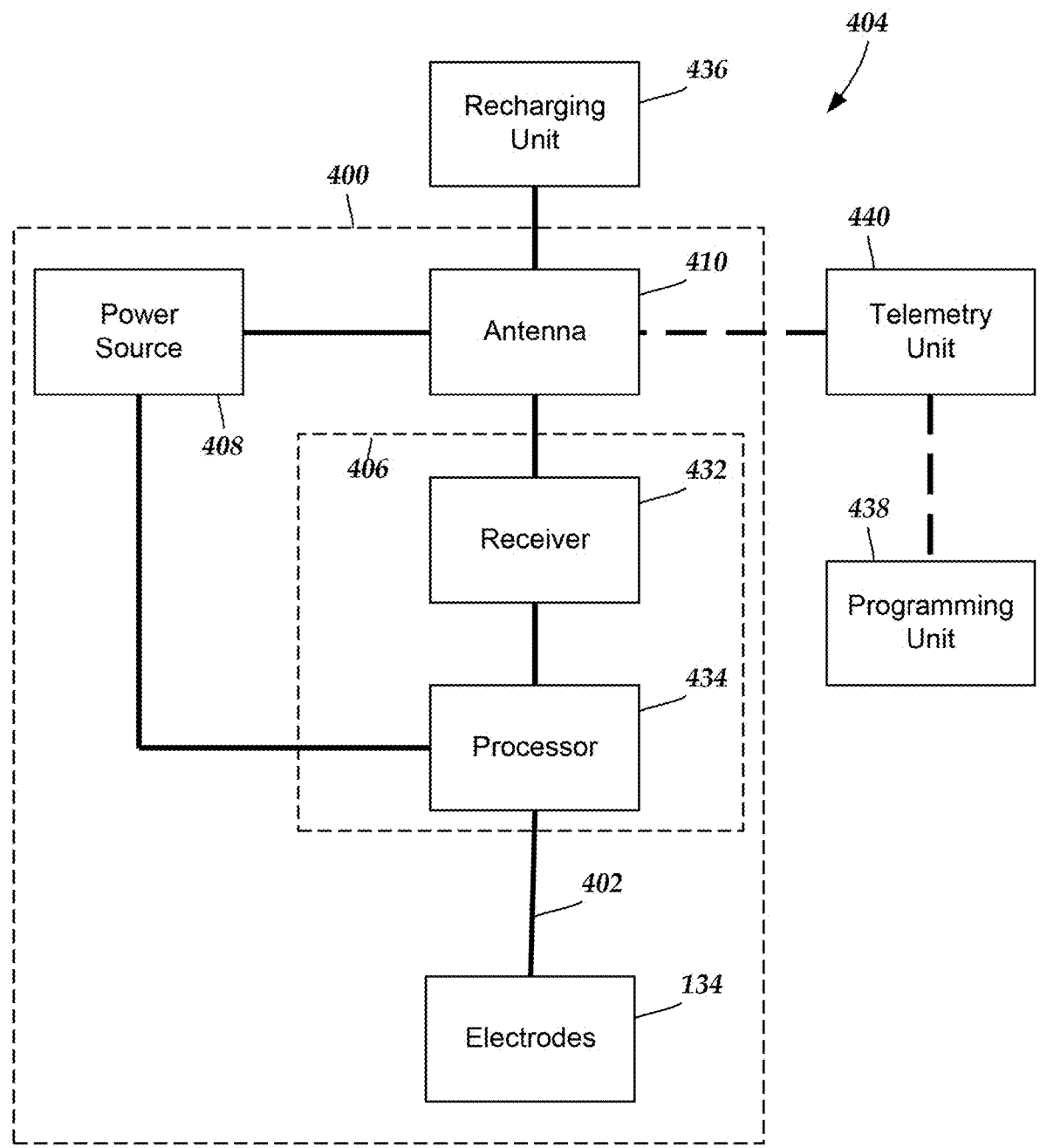
FIG. 4 is a schematic overview of one embodiment of components of an electrical stimulation arrangement, according to the invention.

FIG. 4 is a schematic overview of one embodiment of components of an electrical stimulation arrangement 404 that includes an electrical stimulation system 400 with a lead 402, stimulation circuitry 406, a power source 408, and an antenna 410. The electrical stimulation system can be, for example, any of the electrical stimulation systems described above. It will be understood that the electrical stimulation arrangement can include more, fewer, or different components and can have a variety of different configurations including those configurations disclosed in the stimulator references cited herein.

If the power source 408 is a rechargeable battery or chargeable capacitor, the power source may be recharged/charged using the antenna 410, if desired. Power can be provided for recharging/charging by inductively coupling the power source 408 through the antenna 410 to a recharging unit 436 external to the user. Examples of such arrangements can be found in the references identified above.

In at least some embodiments, electrical current is emitted by the electrodes (such as electrodes 134 in FIG. 1) on the lead 402 to stimulate nerve fibers, muscle fibers, or other body tissues near the electrical stimulation system. The stimulation circuitry 406 can include, among other components, a processor 434 and a receiver 432. The processor 434 is generally included to control the timing and electrical characteristics of the electrical stimulation system. For example, the processor 434 can, if desired, control one or more of the timing, frequency, strength, duration, and waveform of the pulses. In addition, the processor 434 can select which electrodes can be used to provide stimulation, if desired. In some embodiments, the processor 434 selects which electrode(s) are cathodes and which electrode(s) are anodes. In some embodiments, the processor 434 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 438 that, for example, allows modification of pulse characteristics. In the illustrated embodiment, the processor 434 is coupled to a receiver 432 which, in turn, is coupled to the antenna 410. This allows the processor 434 to receive instructions from an external source to, for example, direct the pulse characteristics and the selection of electrodes, if desired.

In at least some embodiments, the antenna 410 is capable of receiving signals (e.g., RF signals) from an external telemetry unit 440 that is programmed by the programming unit 438. The programming unit 438 can be external to, or part of, the telemetry unit 440. The telemetry unit 440 can be a device that is worn on the skin of the user or can be carried by the user and can have a form similar to a pager, cellular phone, or remote control, if desired. As another alternative, the telemetry unit 440 may not be worn or carried by the user but may only be available at a home station or at a clinician's office. The programming unit 438 can be any unit that can provide information to the telemetry unit 440 for transmission to the electrical stimulation system 400. The programming unit 438 can be part of the telemetry unit 440 or can provide signals or information to the telemetry unit 440 via a wireless or wired connection. One example of a suitable programming unit is a computer operated by the user or clinician to send signals to the telemetry unit 440.

The signals sent to the processor 434 via the antenna 410 and the receiver 432 can be used to modify or otherwise direct the operation of the electrical stimulation system 400. For example, the signals may be used to modify the pulses of the electrical stimulation system such as modifying one or more of pulse duration, pulse frequency, pulse waveform, and pulse strength. The signals may also direct the electrical stimulation system 400 to cease operation, to start operation, to start charging the battery, or to stop charging the battery.

Optionally, the electrical stimulation system 400 may include a transmitter (not shown) coupled to the processor 434 and the antenna 410 for transmitting signals back to the telemetry unit 440 or another unit capable of receiving the signals. For example, the electrical stimulation system 400 may transmit signals indicating whether the electrical stimulation system 400 is operating properly or not or indicating when the battery needs to be charged or the level of charge remaining in the battery. The processor 434 may also be capable of transmitting information about the pulse characteristics so that a user or clinician can determine or verify the characteristics.

Although electrical stimulation of tissue has demonstrated effectiveness for many medical conditions, there can be side-effects to electrical stimulation. For example, vagus nerve stimulation, which has been explored as a treatment for heart failure and other medical conditions, may cause undesirable laryngeal muscle activation under some stimulation conditions. Multi-electrode leads may enable greater selectivity of nerve fibers which may be modulated, for example, by using current steering to target areas of nerve bundles. Although multi-electrode leads may provide improved therapy, there can be a challenge in determining which electrodes and stimulation parameters provide therapeutic benefit while reducing or eliminating side effects.

In at least some instances, a treating physician may wish to tailor the stimulation parameters (such as which one or more of the stimulating electrode contacts to use, the stimulation pulse amplitude (such as current or voltage amplitude depending on the stimulator being used,) the stimulation pulse width, the stimulation frequency, the duty cycle, the stimulation phase, or the like or any combination thereof) for a particular patient to improve the effectiveness of the therapy. Examples of stimulation parameters to achieve a particular therapeutic effect or to block a particular side effect can be found in, for example, U.S. Patent Application Publication No. 2015/0202446, incorporated herein by reference, as well as other references cited herein. Electrical stimulation systems can provide an interface that facilitates testing of different sets of stimulation parameters to facilitate parameter selection.

In at least some embodiments, a programmer or clinician seeks to provide more effective stimulation while reducing or avoiding side effects. Methods and systems for identifying stimulation parameters to achieve these objectives are described herein.

Figure 5:
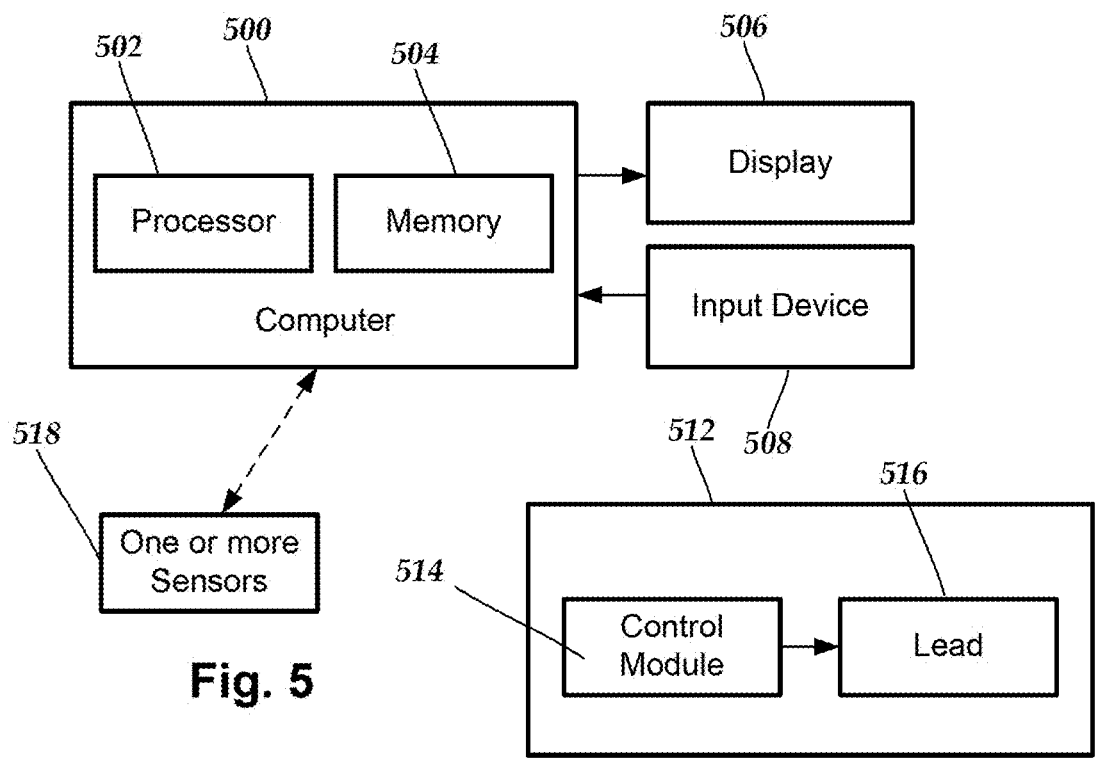
FIG. 5 is a schematic overview of one embodiment of components of a system for selection of stimulation parameters, according to the invention.

FIG. 5 illustrates one embodiment of a system for practicing the invention. The system can include a computer 500 or any other similar device that includes a processor 502 and a memory 504, a display 506, an input device 508, the electrical stimulation system 512, and, optionally, one or more sensors 518 (which may be independent of the electrical stimulation system or part of the electrical stimulation system).

Figure 8:
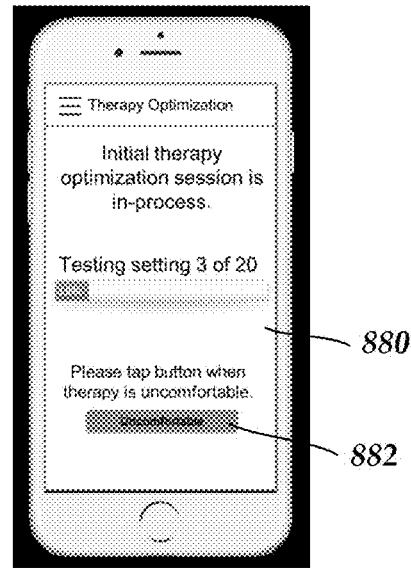
FIG. 8 is a schematic diagram of one embodiment of an interface for performing at least a portion of method of selecting stimulation parameters, according to the invention
Figure 9:
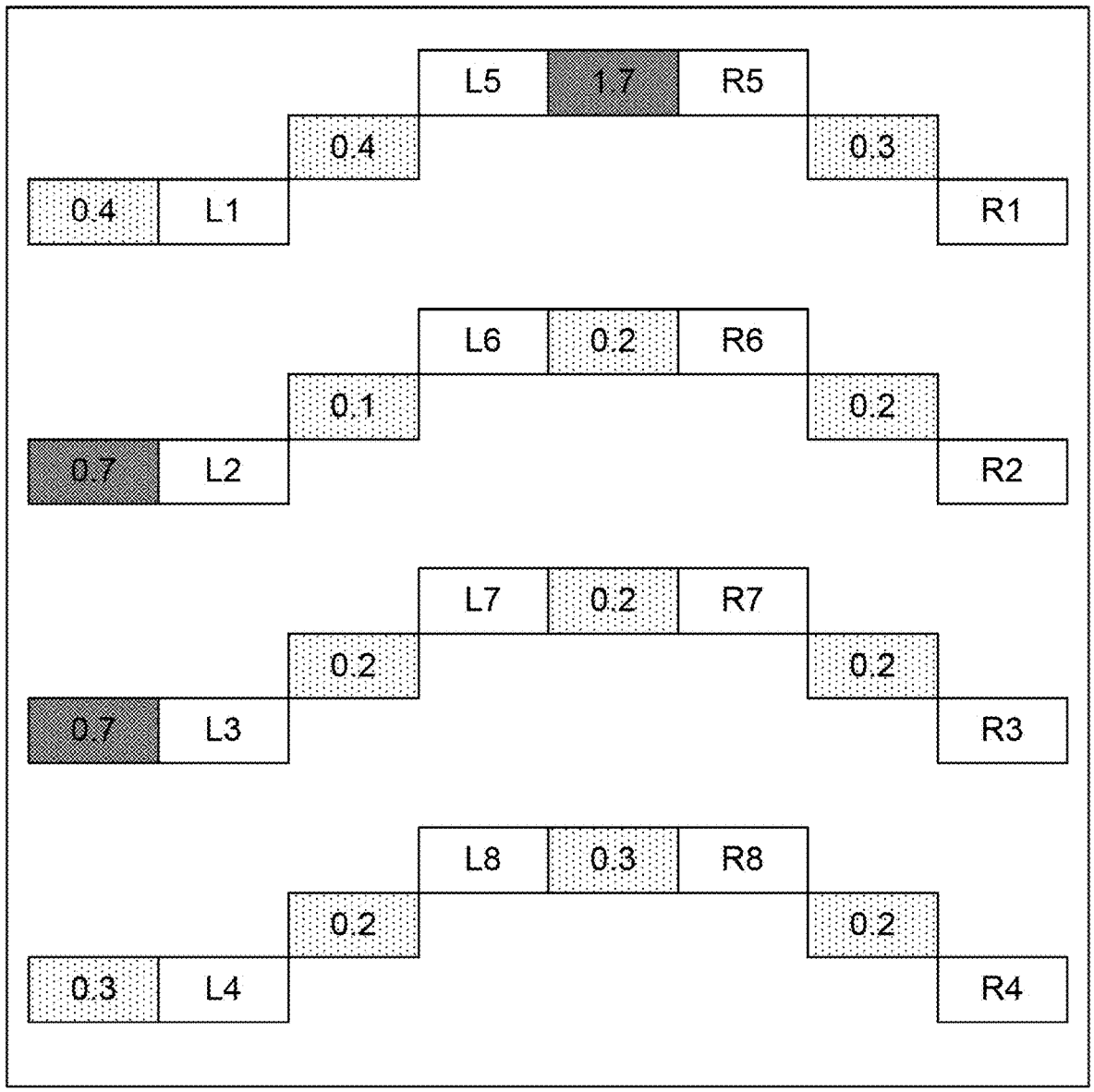
FIG. 9 is a schematic diagram of one embodiment of an interface to assist in a method of selecting stimulation parameters, according to the invention.
Figure 10:
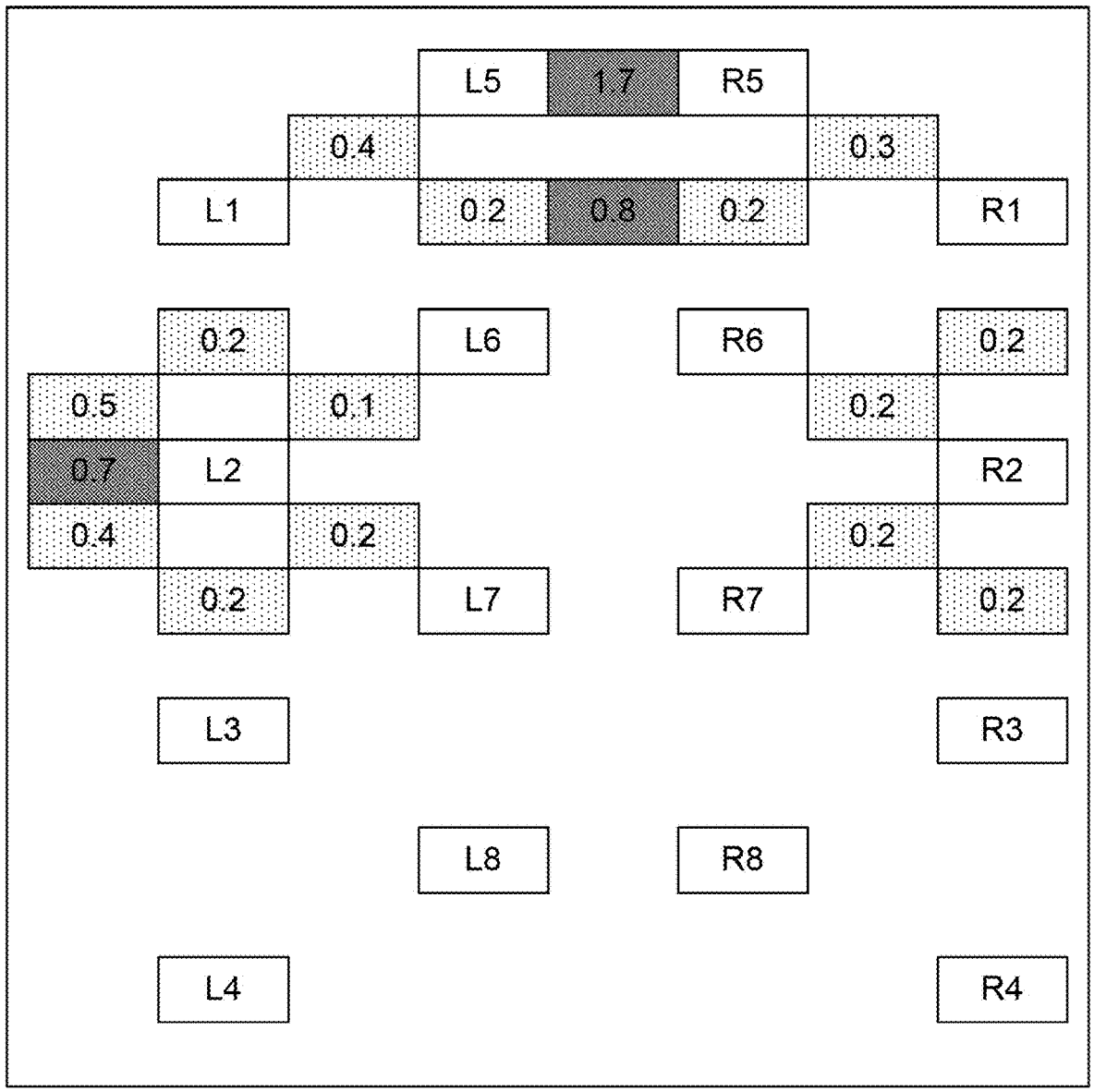
FIG. 10 is a schematic diagram of one embodiment of another interface to assist in a method of selecting stimulation parameters, according to the invention.

The computer 500 can be a laptop computer, desktop computer, tablet, mobile device, smartphone or other devices that can run applications or programs, or any other suitable device for processing information and for presenting a user interface (such as the user interfaces of FIGS. 8, 9, and 10). The computer can be, for example, a clinician programmer, patient programmer, or remote programmer for the electrical stimulation system 512. The computer 500 can be local to the user or can include components that are non-local to the user including one or both of the processor 502 or memory 504 (or portions thereof). For example, in some embodiments, the user may operate a terminal that is connected to a non-local computer. In other embodiments, the memory can be non-local to the user.

The computer 500 can utilize any suitable processor 502 including one or more hardware processors that may be local to the user or non-local to the user or other components of the computer. The processor 502 is configured to execute instructions provided to the processor, as described below.

Any suitable memory 504 can be used for the computer 502. The memory 504 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 506 can be any suitable display device, such as a monitor, screen, display, or the like, and can include a printer. The input device 508 can be, for example, a keyboard, mouse, touch screen, track ball, joystick, voice recognition system, or any combination thereof, or the like and can be used by the user to interact with a user interface or clinical effects map.

The electrical stimulation system 512 can include, for example, a control module 514 (for example, an implantable pulse generator) and a lead 516. The lead can be any suitable lead for peripheral nerve stimulation including, but not limited to the cuff leads illustrated in FIG. 1 and FIGS. 3A-3D. The electrical stimulation system 512 may communicate with the computer 500 through a wired or wireless connection or, alternatively or additionally, a user can provide information between the electrical stimulation system 512 and the computer 500 using a computer-readable medium or by some other mechanism. In some embodiments, the computer 500 may include part of the electrical stimulation system.

The one or more sensors 518 can be any suitable sensor for measuring or observing physiological or other responses to the stimulation. In at least some embodiments, at least one of the sensors 518 is external to the electrical stimulation system. In at least some embodiments, at least one of the sensors 518 is part of the electrical stimulation system, for example, a sensor (e.g., an electrode) disposed on the lead 516 or within the control module 514 or a sensor coupled to the control module 514 through another lead or the like. Examples of physiological or other responses that can be measured or observed include, but are not limited to, muscle electrical potentials, nerve action potentials, heart rate, pulmonary function (e.g., respiratory rate, tidal volume, minute ventilation, or the like), heart sounds such as the first heart sound (S1) or the second heart sound (S2), ECG signals (e.g., R-wave height, Q-R interval, P-interval, or the like), heart rate variability, peripheral temperature, blood pressure (e.g., diastolic, systolic, or mean blood pressure), acetylcholine or catecholamine measurements, accelerometer measurements (e.g., to observe epilepsy, Parkinsonism, or tremor), posture, gait, or the like or any combination thereof.

The present systems and methods can be used to provide stimulation to any suitable target. In particular, the present systems and methods are adapted for stimulating peripheral nerves (e.g., nerves outside of the spinal cord.) One example is vagus nerve stimulation which can be used to treat a variety of disorders or diseases including, but not limited to, heart failure, epilepsy, migraine, or inflammatory diseases. One possible side-effect of vagus nerve stimulation is laryngeal stimulation. Other side effects of peripheral nerve stimulation can be, for example, pain or discomfort. Other types of peripheral nerve stimulation include, but are not limited to, stimulation of the trigeminal nerve, sciatic nerve, femoral nerve, or the like.

Nerves can have complicated anatomy with various fibers and other cells extending along the nerve or portions of the nerve. For example, in targets such as the vagus nerve, the neuroanatomy is not predictable from patient-to-patient, and not even within a patient along the length of the nerve. Orientation of nerve fibers can change significantly longitudinally along the length of the nerve. Therefore, it may be difficult to accurately predict the effects of stimulation using a multi-electrode lead, such as those described above. An advantage of using such multi-electrode leads, however, is that they may be capable of stimulating efficacious regions of the nerve while avoiding, at least in part, regions that produce side effects. A multi-electrode lead with multiple independent current control, offers the capability to target specific locations within a structure (for example, to target nerve fibers contributing to a cardiac effect. A challenge, however, is determining where to target current in a peripheral nerve to avoid or reduce the side effects and maintain or improve efficacy of the stimulation therapy. The present systems and methods are useful for identifying electrodes and stimulation parameters of such complicated and unpredictable anatomy and response.

Figure 6:
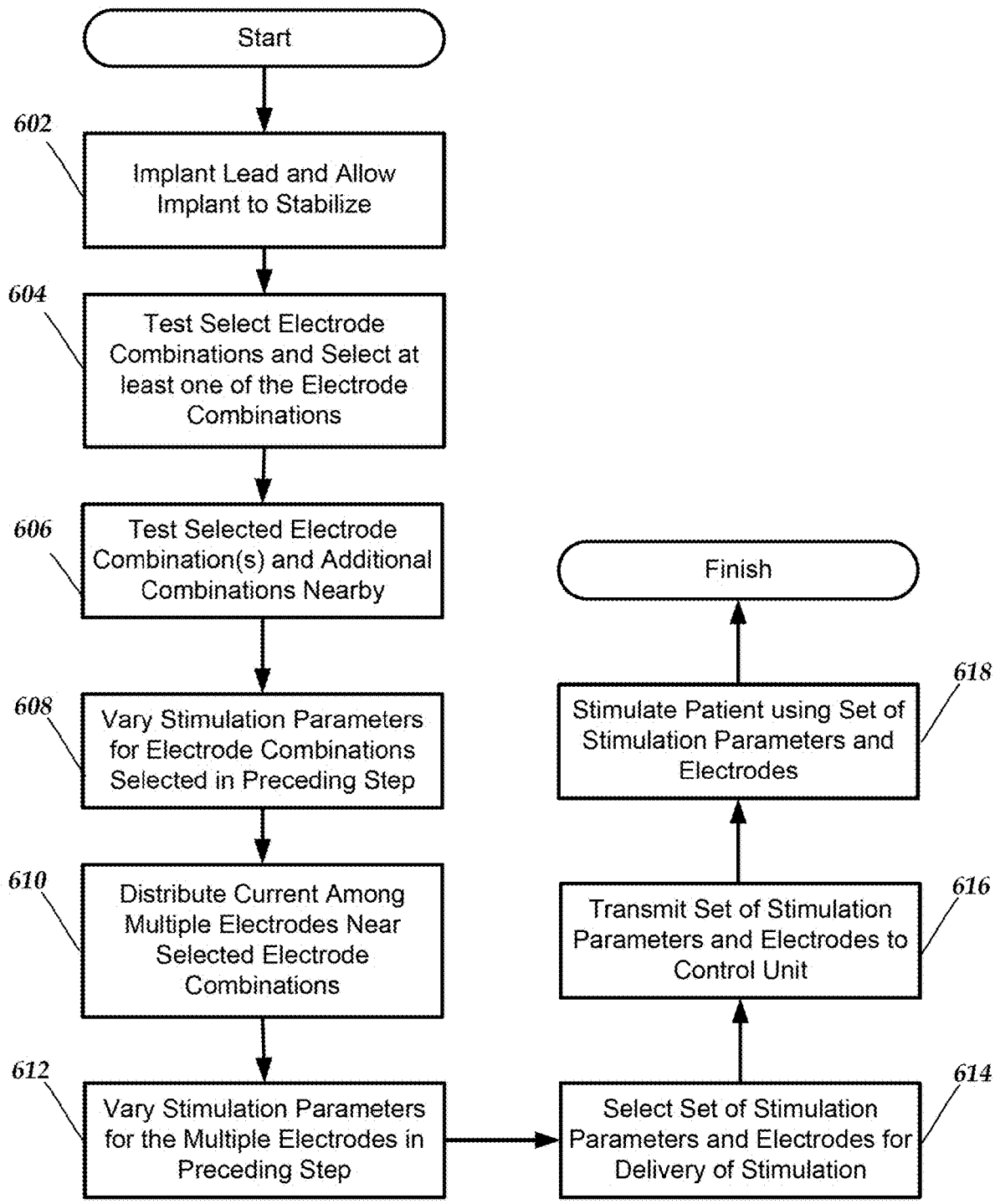
FIG. 6 is a schematic flowchart of one embodiment of a method for selection of stimulation parameters, according to the invention.

FIG. 6 illustrates an embodiment of a method for selecting stimulation parameters for peripheral nerve electrical stimulation. It will be understood that such methods may also be useful for selecting stimulation parameters for other types of electrical stimulation. In step 602, the lead is implanted adjacent or around a peripheral nerve and allowed to stabilize. The stabilization period may be, for example, a few hours or days.

In step 604, an initial set of different electrode combinations are tested to identify locations on the peripheral nerve that, when stimulated, produce beneficial stimulation effects or side effects. In at least some embodiments, the electrode combination includes an electrode pair; however, other embodiments may include three, four, or more electrodes in each electrode combination. The number of electrodes in each electrode combination can be the same or can be different. It will also be recognized that the individual electrodes of the electrode combination can be designated as anodes or cathodes. In some embodiments, the electrodes of the electrode combination can all be anodes or can all be cathodes with the case of the control module acting as the cathode or anode, respectively.

The testing includes receiving or determining, as testing results, one or more values indicative of electrical stimulation using the electrode combination. The values can be numerical or other quantitative values or can be alphanumeric qualitative values or can be simply an indication that the particular stimulation is acceptable or not. In view of the testing results, particular electrodes pairs from the initial set can be identified as indicating regions of the nerve that should be investigated further.

In at least some embodiments, beneficial stimulation effect thresholds (for example, when a beneficial stimulation effect is observed or reaches a threshold level) or side effect thresholds (for example, when a side effect is observed or reaches a threshold level) or both for the electrode combinations can be determined. In some embodiments, the electrode combinations are tested to determine at what stimulation amplitude a side effect manifests or reaches a threshold level (which may be quantitative or subjective.) In at least some embodiments, the objective of this initial set of electrode combinations is to provide a high-level initial mapping of the nerve response and nerve structure that can be refined is later steps.

Figure 7:
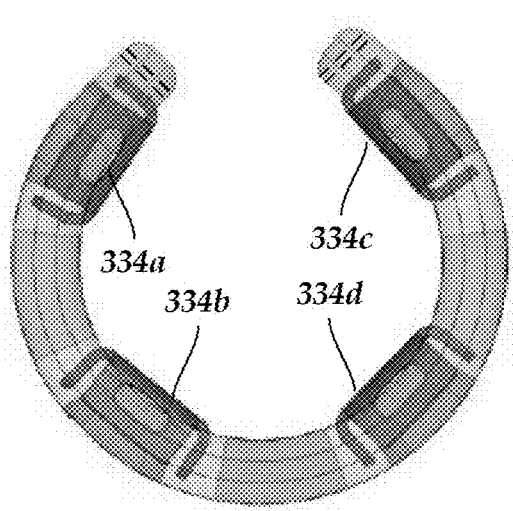
FIG. 7 is a schematic cross-sectional view of one embodiment of a cuff lead, according to the invention.

As an example, a cross-section of one embodiment of a cuff lead is provided in FIG. 7 with four identified electrodes 334a, 334b, 334c, 334d. This cross-section represents one set of electrodes at a particular position along the cuff lead. Referring to FIGS. 3A-3D, the cuff lead 306 includes four sets of electrodes at four different positions along the cuff lead. In one example of step 604, the initial set of different electrodes can be each pair of adjacent electrodes. For the lead and set of electrodes in FIG. 7, this would produce four pairs of electrodes: 1) electrodes 334a, 334b; 2) electrodes 334b, 334c; 3) electrodes 334c, 334d; and 4) electrodes 334d, 334a. In addition, for the cuff lead of 306, there would be four pairs at each of the four positions along the lead, resulting in sixteen pairs in the initial set of electrode combinations to be tested in step 604. In other examples, the initial set of electrode combinations can include electrode pairs containing electrodes that are of different sets, but are adjacent to each other. Any other suitable selection of the initial set of electrode combinations can be used; those selections presented in this paragraph are non-limiting examples.

It will be recognized that other selections of electrode combinations can be made. For example, only electrode combinations at two of the positions along the cuff lead 306 might be tested. The selection of electrode combinations for the initial set may be pre-programmed for an electrical stimulation system or may be selectable by a clinician, user, or other individual (although there may also be a default set of electrode combinations that can be modified.) In at least some embodiments, the initial set of electrode combinations is selected or pre-programmed so that each electrode of the lead is part of no more than one or two of the electrode combinations.

Each electrode combination is tested with one electrode acting as the anode and the other electrode acting as the cathode. In at least some embodiments, the electrode combination may be tested at different stimulation amplitudes. For example, the stimulation amplitude may be stepped up from an initial value by regular (or irregular) increments. At each stimulation amplitude, the presence or absence of (and, optionally, quantitative or subjective level) of a beneficial stimulation effect, side effect(s), or both may be determined. The determination may be made using one or more sensors, user (e.g., patient or clinician) feedback, clinician or programmer observation, or any combination thereof or any other mechanism for detecting beneficial stimulation effects or side effects. In at least some embodiments, the stimulation amplitude is increased until a stop criterion is met. Examples of stop criteria include, but are not limited to, a side effect is observed, the beneficial impact of the therapy has plateaued, a tolerance is reached or exceeded, a stimulation amplitude maximum is reached, or a patient, clinician, or programmer determines to halt the increase of stimulation amplitude, or any combination of these criteria. A system may include all or only some of these criteria.

FIG. 8 illustrates one embodiment of a relatively simple interface 880 that can be used to test the initial set of electrode combinations. In this particular case, such an interface may be suitable for use by the patient with or without a clinician guiding the process. In this system and interface, each of the electrode combinations (twenty electrode combinations in the illustrated example) is sequentially tested with the stimulation amplitude increasing incrementally. For each electrode combination, the user taps the button 882 when the therapy becomes uncomfortable (e.g., produces a discomfort side effect above a subjective threshold.) Once that occurs (or if the stimulation amplitude reaches a maximum stimulation amplitude without the user tapping the button 882), the system continues to the next electrode combination until all of the electrode combinations have been tested.

It will be understood that other interfaces can be used including, but not limited to those that are operated by a clinician or device programmer. Examples of other interfaces that may be used to select electrodes and stimulation amplitudes can be found at, for example, U.S. patent application Ser. Nos. 12/454,330; 12/454,312; 12/454,340; 12/454,343; and 12/454,314 and U.S. Patent Application Publication No. 2014/0277284, all of which are incorporated herein by reference in their entireties.

In some embodiments, the testing of each electrode combination proceeds automatically and the system moves from one electrode combination to the next automatically. Optionally, the user may have the option to halt or pause the system. In other embodiments, the user can direct the individual testing of electrode combinations. Optionally, the user may be allowed to skip electrode combinations.

FIG. 9 illustrates one embodiment of an interface that can present the results of the testing. In the interface, the sixteen electrodes are identified as L1-L8 and R1-R8. The sixteen electrodes can correspond to, for example, the sixteen electrodes on the cuff lead 305 of FIGS. 3A-3D. The side effect threshold values are reported in the other boxes (ranging in this example from 0.1 to 1.7 mA). The boxes to the left of L1-L4 correspond to the electrode combination of L1-L4 with R1-R4 respectively. The other result boxes are disposed between the two electrodes of the pair. It will be understood that values other than side effect threshold values may be determined and illustrated or that multiple values for each pair may be determined and illustrated.

In at least some embodiments, determined values that meet threshold criteria are indicated. For example, the boxes containing values that meet threshold criteria may be colored (for example, colored green) or shaded differently than those that do not, as illustrated in FIG. 9. Other visual indications may be used instead of, or in addition to, coloring or shading. In some embodiments, the corresponding electrodes that produced the values may also be indicated by different coloring or shading or any other suitable visual indication. In the example, the boxes with values from 0.7-1.7 mA are indicated because they meet a threshold criterion of achieving at least 0.5 mA prior to reaching an intolerable level of a side effect. Thus, in this case, the electrode combinations 1) L5/R5; 2) L2/R2; and 3) L3/R3 appear to indicate the best regions to continue testing.

In some embodiments, the system automatically determines which electrode combinations to use in the succeeding step. Optionally, the user may be allowed to modify the selection of electrode combinations to add or remove selected electrode combinations. In other embodiments, the user may be directed to select electrode combinations to use in the succeeding steps.

In some embodiments, step 604 can be performed relatively quickly such as, for example, within 10, 15, 20, 30, 45, or 60 minutes or more. In some embodiments, step 604 may be performed solely by the patient using a patient programmer or an application on a mobile device, such as a mobile phone, tablet, or laptop computer.

In step 606, one or more of the electrode combinations selected in step 604, as well as additional electrode combinations, near or adjacent the selected electrode combinations are tested. In some embodiments, each of the additional electrode combinations includes at least one of the electrodes of one of the electrode combinations selected in step 604.

In some embodiments, the system automatically determines which additional electrode combinations to test. Optionally, the user may be allowed to modify the selection of electrode combinations to add or remove selected electrode combinations. In other embodiments, the user may be directed to select the additional electrode combinations.

The testing includes receiving or determining, as testing results, one or more values indicative of electrical stimulation using the electrode combination. The values can be numerical or other quantitative values or can be alphanumeric qualitative values or can be simply an indication that the particular stimulation is acceptable or not.

FIG. 10 illustrates an interface with the results of testing these electrode combinations. As can be seen, in this example, electrode combinations around 1) L5/R5 and 2) L2/R2 have been tested. (The results to the left of L2 correspond to pairs of R1-R3, respectively, from top to bottom. The 0.8 result near the top results from a test of the L5/R6 pair.)

In at least some embodiments, the testing of each electrode combination in step 606 is similar or the same as the testing in step 604. In other embodiments, the testing of each electrode combination in step 606 may include the testing performed in step 604 and also include a longer period of stimulation to observe any longer term or slower developing beneficial stimulation effects or side effects. Alternatively or additionally, one or more physiological responses (for example, measured using one or more of the sensors described above) can be monitored or observed. In some embodiments, a duty cycle may be employed (for example, 20 seconds of stimulation followed by 40 seconds of no stimulation) during the stimulation time. In some embodiments, different duty cycles can be tested. The testing in step 606 may be performed over the course of minutes, hours, days, or weeks.

In step 606, one or more of the tested electrode combinations are selected for further testing. The selection of the electrode combinations may be based on any suitable criterion or set of criteria. For example, a set of criteria may include a) a maximum stimulation amplitude at which stimulation is tolerable (e.g., side effects are tolerable at the maximum stimulation amplitude); b) a minimum amount of beneficial stimulation effect (e.g., at least a threshold amount of beneficial stimulation effect at a tolerable stimulation amplitude); and c) a ratio of desired beneficial stimulation effect to undesired side effect at one or more stimulation amplitudes.

In some embodiments, the system automatically determines which electrode combinations to use in the succeeding step. Optionally, the user may be allowed to modify the selection of electrode combinations to add or remove selected electrode combinations. In other embodiments, the user may be directed to select electrode combinations to use in the succeeding steps.

In step 608, the stimulation parameters are varied for the electrode combinations selected in step 606 to determine the results of different sets of stimulation parameters. Examples of stimulation parameters that can be varied include, but are not limited to, stimulation amplitude, pulse frequency, pulse duration, duty cycle, pulse waveform, electrode polarity (e.g., which electrode is the anode and which is the cathode), burst frequency (where the pulses are delivered in bursts of pulses followed by a period of no pulses), or the like or any combination thereof. The testing in step 608 may be performed over the course of minutes, hours, days, or weeks. For example, stimulation parameters (e.g., stimulation amplitude, stimulation frequency, pulse width, duty cycle, pulse waveform, or the like or any combination thereof) for one electrode of an electrode pair can be held constant while the stimulation parameters for the other electrode are varied. Next, the stimulation parameters for the first electrode can be varied while the stimulation parameters for the second can be held constant (for example, at a predetermined set of parameters or at a selected set of parameters based on the previous sweep of stimulation parameters). In some embodiments, the testing may include switching polarities of the electrodes.

The testing includes receiving or determining, as testing results, one or more values indicative of electrical stimulation using the electrode combination. The values can be numerical or other quantitative values or can be alphanumeric qualitative values or can be simply an indication that the particular stimulation is acceptable or not.

From the testing in step 608, one or more electrode combinations and one or more corresponding sets of stimulation parameters are then selected for further testing. The selection may be based on the use of a suitable (or even best) set of stimulation parameters for the individual electrode combinations. The selection of the electrode combinations may be based on any suitable criterion or set of criteria. For example, a set of criteria may include a) a maximum stimulation amplitude at which stimulation is tolerable (e.g., side effects are tolerable at the maximum stimulation amplitude); b) a minimum amount of beneficial stimulation effect (e.g., at least a threshold amount of beneficial stimulation effect at a tolerable stimulation amplitude); and c) a ratio of desired beneficial stimulation effect to undesired side effect at one or more stimulation amplitudes. In some embodiments, selection criteria may also include consideration of the other stimulation parameters that were tested and whether those stimulation parameters would be suitable for long term stimulation of the patient.

In some embodiments, the system automatically determines which electrode combinations to use in the succeeding step. Optionally, the user may be allowed to modify the selection of electrode combinations to add or remove selected electrode combinations. In other embodiments, the user may be directed to select electrode combinations to use in the succeeding steps.

In step 610, the results for selected electrode combination (s) from step 608 can then be used to expand beyond just pairs of electrodes to test groups of electrodes for delivery of electrical stimulation. The group of electrodes may contain two, three, four or more electrodes where, for example, one or more electrodes act as anodes and one or more electrodes act as cathodes. For example, the anodic or cathodic current could be distributed between two or more electrodes where the division between electrodes can be equal (e.g., 50% on each) or unequal (e.g., split 10%/90%; 20%/80%; 33%/67%; 33%/33%/33%; or any other arrangement.) As an example, utilizing the electrode designations in FIGS. 9 and 10, one arrangement of electrodes includes 100% of the cathodic current on L5, 60% of the anodic current on R5; 35% of the anodic current on L1; and 5% of the anodic current on L6. Such an arrangement will localize the cathodic stimulation near electrode L5 with the anodic electrodes R5, L1, and L6 guarding the cathode and resisting spread of stimulation from that locale. In addition to the electrodes on the cuff lead, in some embodiments, the case of the control module may also be used as an electrode. In at least some embodiments, the distribution of current between the electrodes may be based on the relative beneficial stimulation effect evoked at those electrodes, or the side effects evoked at those electrodes, or both.

Any number of multiple electrode groups can be tested in step 610. The testing in step 610 may be performed over the course of minutes, hours, days, or weeks. The testing includes receiving or determining, as testing results, one or more values indicative of electrical stimulation using the electrode group. The values can be numerical or other quantitative values or can be alphanumeric qualitative values or can be simply an indication that the particular stimulation is acceptable or not.

One or more the tested electrode groups are selected to continue. The selection of the one or more multiple electrode groups may be based on any suitable criterion or set of criteria. For example, a set of criteria may include a) a maximum stimulation amplitude at which stimulation is tolerable (e.g., side effects are tolerable at the maximum stimulation amplitude); b) a minimum amount of beneficial stimulation effect (e.g., at least a threshold amount of beneficial stimulation effect at a tolerable stimulation amplitude); and c) a ratio of desired beneficial stimulation effect to undesired side effect at one or more stimulation amplitudes.

In step 612, the stimulation parameters are varied for the one or more multiple electrode groups selected in step 610 to determine the results of different sets of stimulation parameters. Examples of stimulation parameters that can be varied include, but are not limited to, stimulation amplitude, pulse frequency, pulse duration, duty cycle, pulse waveform, electrode polarity (e.g., which electrode is the anode and which is the cathode), burst frequency (where the pulses are delivered in bursts of pulses followed by a period of no pulses), or the like or any combination thereof. The testing in step 608 may be performed over the course of minutes, hours, days, or weeks.

The testing includes receiving or determining, as testing results, one or more values indicative of electrical stimulation using the electrode group. The values can be numerical or other quantitative values or can be alphanumeric qualitative values or can be simply an indication that the particular stimulation is acceptable or not.

In step 614, one or more multiple electrode groups and one or more corresponding sets of stimulation parameters are then selected for patient stimulation based on the testing in step 612. In step 616, the set of stimulation parameters and selection of electrodes for each of the one or more multiple electrode groups is transmitted or otherwise communicated to the control unit. In step 618, the patient is stimulated using the stimulation parameters and selection of electrodes for at least one of the one or more multiple electrode groups.

In at least some embodiments, portions of the method illustrated in FIG. 6 can be repeated later to modify or enhance the electrical stimulation. For example, steps 612 to 618 (or steps 606 to 618 or steps 604 to 618) may be repeated at regular or irregular intervals to further modify the stimulation parameters. In some instances, the nerve or other tissue affected by stimulation may change over time so that modification of the stimulation parameters or electrode choice or both may enhance stimulation. Moreover, the steps may be part of a closed loop feedback system including the control module and sensors and, optionally, the programming unit to continue to modify the stimulation parameters and selection of electrodes over time.

In some embodiments, the nerve or other tissue affected by stimulation may change with a change in patient posture. In such cases, the steps 612 to 618 (or steps 606 to 618 or steps 604 to 618) may be repeated separately while the patient is in different postures to derive a posture-specific stimulation configuration for each posture. A particular stimulation configuration can then be applied by the control module at any given instance based on a detected patient posture. A set of stimulation parameters can be referred to as a stimulation configuration or stimulation program.

Similarly, different stimulation configurations may be determined for multiple, different physical states based on, for example, level of activity, type of activity, or the like. The physical state may be detected using any of the sensors described above or may be manually selected by the patient or other individual. For example, a physical state may be determined based on type of gait, heart rate, respiration, or the like or any combination thereof.

In some embodiments, different stimulation configurations can be determined for different levels of patient symptoms or conditions (for example, different levels of pain). For example, one stimulation configuration can be determined for little or no pain (for example, this stimulation configuration may be light stimulation or no stimulation at all), another stimulation configuration for moderate pain (for example, a stimulation configuration that produces a beneficial stimulation effect with little or no side effects), and a third stimulation configuration for higher levels of pain (for example, a stimulation configuration that increases the beneficial stimulation effect despite an increase in one or more side effects). The patient symptom or condition may be detected using any of the sensors described above or may be manually selected by the patient or other individual.

In any of the steps 604-614, the selection of electrode combinations or electrode groups may be performed manually or automatically. In some embodiments, machine learning may be used on a system to first train the system to perform the selection using known or user-guided selections and then to allow the system to perform the selections in view of the paradigm created by machine learning. In some embodiments, the process of steps 604-614 may be repeated periodically or may be initiated manually (for example, by a clinician or patient). In some embodiments, when the process may be initiated by the system itself, the process of steps 604-614 may only be initiated if a gating criterion is met. Examples of gating criteria include, but are not limited to, a threshold level of a symptom or condition (for example, a threshold level of pain), a threshold level of patient activity, or the like or any combination thereof.

In some embodiments, it may be useful to identify two or more multiple electrode groups for stimulation. For example, the system may alternate between the different groups to prevent or reduce adaptation of the nerve to the stimulation. Such adaptation may reduce the efficacy of stimulation therapy. For example, the system may alternate between different groups at regular or irregular intervals. Such intervals can be in the range of 1 to 60 minutes, 1 to 24 hours, 1 to 7 days, or any other suitable interval. Alternatively or additionally, the system may switch to a different group at one or more instances such as, for example, when the system determines a drop in therapy efficacy, an increase in side effect, or user direction to switch groups.

Alternatively or additionally, the two or more electrode groups may be operated concurrently (or during overlapping time periods) using the same or different stimulation parameters. This may be useful to provide increased beneficial stimulation effects, to target different symptoms or conditions or produce different beneficial stimulation effects, to produce a beneficial stimulation effect using one electrode group while blocking or reducing a side effect using another electrode group, to activate a portion of the tissue using one electrode group while generating a blocking or inhibiting response in another portion of the tissue using another electrode group, or the like or nay combination thereof.

In some embodiments, the same procedure can be used to not only determine regions to stimulate to achieve therapy, but also regions to stimulate to block or inhibit transmission of signals along the nerve or to deplete of neurotransmitters. These effects may result in therapy or reduce side effects. In at least some embodiments, blocking current is delivered at higher frequencies relative to stimulation current, for example, at frequencies greater than 100 Hz for neurotransmitter depletion or greater than 1 kHz for conduction block, compared to less than 100 Hz for stimulation.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (e.g., RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A method of selecting electrical stimulation parameters for an electrical stimulation device implanted in a patient, the electrical stimulation device comprising an electrical stimulation lead comprising a plurality of electrodes, the method comprising:
    for each of a plurality of first electrode combinations, receiving at least one value indicative of electrical stimulation using the first electrode combination, wherein each of the first electrode combinations comprises at least two electrodes of the electrical stimulation lead;
    based on the received values indicative of electrode stimulation using the first electrode combinations, selecting one or more of the first electrode combinations;
    selecting a plurality of second electrode combinations including the selected one or more of the first electrode combinations and one or more additional electrode combinations, wherein at least one of the additional electrode combinations includes at least one electrode from the selected one or more of the first electrode combinations, wherein each of the second electrode combinations comprises at least two electrodes of the electrical stimulation lead;
    for each of the plurality of second electrode combinations, receiving at least one value indicative of electrical stimulation using the second electrode combination;
    based on the received values indicative of electrode stimulation using the second electrode combinations, selecting one or more of the second electrode combinations;
    for each of the selected one or more of the second electrode combinations, receiving values indicative of electrical stimulation using different sets of stimulation parameters with the selected one or more of the second electrode combinations;
    based on the values indicative of the electrical stimulation using the different sets of stimulation parameters, selecting at least one third electrode combination that includes two or more electrodes of the electrical stimulation lead;
    for each of the selected at least one third electrode combination, receiving values indicative of electrical stimulation using different sets of stimulation parameters with the selected at least one third electrode combination;
    based on the values indicative of the electrical stimulation using the different sets of stimulation parameters, selecting one of the at least one third electrode combination as a final electrode group and selecting one of the different sets of stimulation parameters for the final electrode group; and
    initiating a signal to the electrical stimulation device implanted in the patient, the signal indicating the final electrode group and the selected set of stimulation parameters to be used with the final electrode group for electrical stimulation of the patient through the electrical stimulation lead using the final electrode group and the selected set of stimulation parameters.

2. The method of claim 1, further comprising stimulating the patient using the final electrode group and the selected set of stimulation parameters.

3. The method of claim 1, further comprising
    based on the values indicative of the electrical stimulation using the different sets of stimulation parameters, selecting one of the at least one third electrode combination as a second final electrode group and selecting one of the sets of stimulation parameters for the second final electrode group; and
    initiating a signal to the electrical stimulation device implanted in the patient, the signal indicating the second final electrode group and the selected set of stimulation parameters to be used with the second final electrode group for electrical stimulation of the patient through the electrical stimulation lead using the second final electrode group and the selected set of stimulation parameters.

4. The method of claim 3, further comprising
    stimulating the patient using the final electrode group and the selected set of stimulation parameters for the final electrode group; and
    switching to stimulating the patient using the second final electrode group and the selected set of stimulation parameters for the second final electrode group.

5. The method of claim 3, further comprising alternating between stimulating the patient using the final electrode group and the selected set of stimulation parameters for the final electrode group and stimulating the patient using the second final electrode group and the selected set of stimulation parameters for the second final electrode group.

6. The method of claim 1, wherein receiving at least one value indicative of electrical stimulation using the first electrode combination comprises receiving from the patient an indication of a threshold stimulation amplitude, wherein stimulation at tested stimulation amplitudes below the threshold stimulation amplitude is tolerable to the patient, but stimulation at the threshold stimulation amplitude is not tolerable to the patient.

7. The method of claim 1, wherein receiving at least one value indicative of electrical stimulation using the first electrode combination comprises receiving from the patient an indication of a threshold stimulation amplitude, wherein stimulation at tested stimulation amplitudes above the threshold stimulation amplitude is not tolerable to the patient, but stimulation at the threshold stimulation amplitude is tolerable to the patient.

8. The method of claim 1, wherein the set of stimulation parameters comprises at least one of stimulation amplitude, pulse frequency, pulse duration, duty cycle, pulse waveform, electrode polarity, or burst frequency.

9. The method of claim 1, wherein at least one of the at least one third electrode combination comprises at least three electrodes, wherein either a) at least two electrodes are anodes or b) at least two electrodes are cathodes or c) both a) and b).

10. The method of claim 1, wherein at least one of the at least one third electrode combination comprises an electrode comprising a case of a control unit of the electrical stimulation device.

11. The method of claim 1, wherein each of the at least one third electrode combination comprises at least two electrodes of a one of the selected one or more of the second electrode combinations.

12. The method of claim 1, wherein no electrode of the electrical stimulation lead is part of more than two of the first electrode combinations.

13. A system for selecting stimulation parameters for electrical stimulation, the system comprising:
a processor configured and arranged to perform actions, the actions comprising:
for each of a plurality of first electrode combinations, receiving at least one value indicative of electrical stimulation using the first electrode combination, wherein each of the first electrode combinations comprises at least two electrodes of the electrical stimulation lead;
based on the received values indicative of electrode stimulation using the first electrode combinations, selecting one or more of the first electrode combinations;
selecting a plurality of second electrode combinations including the selected one or more of the first electrode combinations and one or more additional electrode combinations, wherein at least one of the additional electrode combinations includes at least one electrode from the selected one or more of the first electrode combinations, wherein each of the second electrode combinations comprises at least two electrodes of the electrical stimulation lead;
for each of the plurality of second electrode combinations, receiving at least one value indicative of electrical stimulation using the second electrode combination;
based on the received values indicative of electrode stimulation using the second electrode combinations, selecting one or more of the second electrode combinations;
for each of the selected one or more of the second electrode combinations, receiving values indicative of electrical stimulation using different sets of stimulation parameters with the selected one or more of the second electrode combinations;
based on the values indicative of the electrical stimulation using the different sets of stimulation parameters, selecting at least one third electrode combination that includes two or more electrodes of the electrical stimulation lead;
for each of the selected at least one third electrode combination, receiving values indicative of electrical stimulation using different sets of stimulation parameters with the selected at least one third electrode combination;
based on the values indicative of the electrical stimulation using the different sets of stimulation parameters, selecting one of the at least one third electrode combination as a final electrode group and selecting one of the different sets of stimulation parameters for the final electrode group; and
initiating a signal to the electrical stimulation device implanted in the patient, the signal indicating the final electrode group and the selected set of stimulation parameters to be used with the final electrode group for electrical stimulation of the patient through the electrical stimulation lead using the final electrode group and the selected set of stimulation parameters.

14. The system of claim 13, further comprising an implantable stimulation device configured and arranged to stimulate the patient using the final electrode group and the selected set of stimulation parameters for the final electrode group.

15. The system of claim 13, wherein receiving at least one value indicative of electrical stimulation using the first electrode combination comprises receiving from the patient an indication of a threshold stimulation amplitude, wherein stimulation at tested stimulation amplitudes below the threshold stimulation amplitude is tolerable to the patient, but stimulation at the threshold stimulation amplitude is not tolerable to the patient.

16. The system of claim 13, wherein receiving at least one value indicative of electrical stimulation using the first electrode combination comprises receiving from the patient an indication of a threshold stimulation amplitude, wherein stimulation at tested stimulation amplitudes above the threshold stimulation amplitude is not tolerable to the patient, but stimulation at the threshold stimulation amplitude is tolerable to the patient.

17. The system of claim 13, wherein the set of stimulation parameters comprises at least one of stimulation amplitude, pulse frequency, pulse duration, duty cycle, pulse waveform, electrode polarity, or burst frequency.

18. A non-transitory computer-readable medium having processor-executable instructions for selecting stimulation parameters for electrical stimulation, the processor-executable instructions, when installed onto a device, enable the device to perform actions, the actions comprising:
for each of a plurality of first electrode combinations, receiving at least one value indicative of electrical stimulation using the first electrode combination, wherein each of the first electrode combinations comprises at least two electrodes of the electrical stimulation lead;
based on the received values indicative of electrode stimulation using the first electrode combinations, selecting one or more of the first electrode combinations;
selecting a plurality of second electrode combinations including the selected one or more of the first electrode combinations and one or more additional electrode combinations, wherein at least one of the additional electrode combinations includes at least one electrode from the selected one or more of the first electrode combinations, wherein each of the second electrode combinations comprises at least two electrodes of the electrical stimulation lead;
for each of the plurality of second electrode combinations, receiving at least one value indicative of electrical stimulation using the second electrode combination;
based on the received values indicative of electrode stimulation using the second electrode combinations, selecting one or more of the second electrode combinations;

for each of the selected one or more of the second electrode combinations, receiving values indicative of electrical stimulation using different sets of stimulation parameters with the selected one or more of the second electrode combinations;

based on the values indicative of the electrical stimulation using the different sets of stimulation parameters, selecting at least one third electrode combination that includes two or more electrodes of the electrical stimulation lead;

for each of the selected at least one third electrode combination, receiving values indicative of electrical stimulation using different sets of stimulation parameters with the selected at least one third electrode combination;

based on the values indicative of the electrical stimulation using the different sets of stimulation parameters, selecting one of the at least one third electrode combination as a final electrode group and selecting one of the different sets of stimulation parameters for the final electrode group; and initiating a signal to the electrical stimulation device implanted in the patient, the signal indicating the final electrode group and the selected set of stimulation parameters to be used with the final electrode group for electrical stimulation of the patient through the electrical stimulation lead using the final electrode group and the selected set of stimulation parameters.

19. The computer-readable medium of claim 18, wherein receiving at least one value indicative of electrical stimulation using the first electrode combination comprises receiving from the patient an indication of a threshold stimulation amplitude, wherein stimulation at tested stimulation amplitudes below the threshold stimulation amplitude is tolerable to the patient, but stimulation at the threshold stimulation amplitude is not tolerable to the patient.

20. The computer-readable medium of claim 18, wherein receiving at least one value indicative of electrical stimulation using the first electrode combination comprises receiving from the patient an indication of a threshold stimulation amplitude, wherein stimulation at tested stimulation amplitudes above the threshold stimulation amplitude is not tolerable to the patient, but stimulation at the threshold stimulation amplitude is tolerable to the patient.

\* \* \* \* \*